(12) United States Patent
Hamprecht et al.

(10) Patent No.: US 6,525,000 B1
(45) Date of Patent: Feb. 25, 2003

(54) METHOD FOR PRODUCING ANELLATED TRIAZOLES AND NEW ANELLATED TRIAZOLES AND THEIR USE

(75) Inventors: Gerhard Hamprecht, Weinheim (DE); Olaf Menke, Altleiningen (DE); Robert Reinhard, Ludwigshafen (DE); Peter Schäfer, Ottersheim (DE); Cyrill Zagar, Ludwigshafen (DE); Martina Otten, Ludwigshafen (DE); Karl-Otto Westphalen, Speyer (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/719,812

(22) PCT Filed: Jun. 29, 1999

(86) PCT No.: PCT/EP99/04482

§ 371 (c)(1),
(2), (4) Date: Dec. 18, 2000

(87) PCT Pub. No.: WO00/01700

PCT Pub. Date: Jan. 13, 2000

(30) Foreign Application Priority Data

Jul. 3, 1998 (DE) .......................................... 198 29 745

(51) Int. Cl.⁷ .................... C07D 498/04; C07D 513/04; C07D 487/04; A01N 43/90
(52) U.S. Cl. ...................... 504/222; 504/223; 504/228; 544/10; 544/64; 544/184; 564/36
(58) Field of Search ................................. 504/222, 223, 504/228; 544/10, 64, 184; 564/36

(56) References Cited

U.S. PATENT DOCUMENTS

| | | | |
|---|---|---|---|
| 4,789,394 A | 12/1988 | Böhner et al. ................. | 71/67 |
| 5,605,898 A | * | 2/1997 | Schafer et al. ........... 514/229.2 |

OTHER PUBLICATIONS

Carey, F.A. et al, "Advanced Organic Chemistry, Part B." 1983, Plenum Press, New York, pp. 58–60.*

* cited by examiner

Primary Examiner—Mukund J. Shah
Assistant Examiner—Thomas McKenzie
(74) Attorney, Agent, or Firm—Keil & Weinkauf

(57) ABSTRACT

A process for preparing fused triazoles of formula I

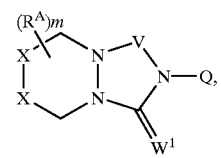

where:
  X—X is C—O, C—S, C—SO, C—SO$_2$, or C—NR$^1$;
  V is C=W$^2$, R$^1$R$^2$C—C(=W$^2$)— or C(=V$^2$)—C (=W$^2$);
  W$^1$, W$^2$ are oxygen or sulfur;
which comprises reacting substituted N-aminoureas are reacted with formaldehyde or paraformaldehyde to give the corresponding methyleneimino ureas; cyclizing these in the presence of catalytic amounts of acid or metal oxide to give tetrahydro-4H-1,3,4-oxa(or thia)diazines, and cyclizing the fused triazoles using phosgene or a phosgene substitute. Also disclosed are novel fused triazoles of the formula I'

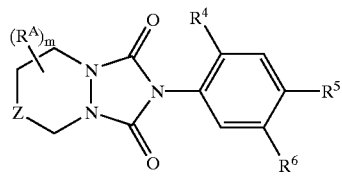

11 Claims, No Drawings

METHOD FOR PRODUCING ANELLATED TRIAZOLES AND NEW ANELLATED TRIAZOLES AND THEIR USE

The present invention relates to a process for preparing fused triazoles of the formula I

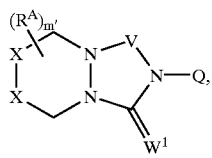

I where:
X—X is C—O, C—S, C—SO, C—CO$_2$ or C—NR$^1$;
V is C=W$^2$, R$^1$R$^2$C—C(=W$^2$)— or C(=W$^2$)—C(=W$^2$);
W$^1$, W$^2$ are oxygen or sulfur;
R$^A$ is hydrogen, hydroxyl, COOH, COOR$^2$, halogen, cyano, C(O)NR$^{11}$R$^{12}$, OR$^3$, C$_1$–C$_6$-alkyl, C$_1$–C$_6$-haloalkyl, C$_3$–C$_6$-alkenyl, C$_3$–C$_6$-alkynyl, COR$^3$, S(O)$_n$R$^3$ or C(O)SR$^2$;
R$^1$ is hydrogen, hydroxyl, halogen, CN, C$_1$–C$_6$-alkyl, C$_1$–C$_6$-haloalkyl, C$_2$–C$_6$-alkenyl, C$_2$–C$_6$-alkynyl, COR$^3$, CHO, OR$^3$, COOR$^2$, C(O)SR$^2$, C(O)NR$^{11}$R$^{12}$;
R$^2$ is hydrogen, C$_1$–C$_6$-alkyl, C$_1$–C$_6$-haloalkyl, C$_2$–C$_6$-alkenyl or C$_2$–C$_6$-alkynyl;
R$^3$ is C$_1$–C$_6$-alkyl, C$_3$–C$_6$-cycloalkyl, C$_2$–C$_6$-alkenyl, C$_2$–C$_6$-alkynyl, C$_1$–C$_6$-haloalkyl, C$_1$–C$_6$-alkoxy-C$_1$–C$_6$-alkyl, carboxyl-C$_1$–C$_6$-alkyl, C$_1$–C$_6$-alkoxycarbonyl-C$_1$–C$_6$-alkyl, C$_1$–C$_6$-alkylthio-C$_1$–C$_6$-alkyl, C$_1$–C$_6$-alkylsulfinyl-C$_1$–C$_6$-alkyl, C$_1$–C$_6$-alkylsulfonyl-C$_1$–C$_6$-alkyl, C$_3$–C$_6$-cycloalkyl-C$_1$–C$_6$-alkyl, C$_3$–C$_6$-alkenyloxycarbonyl-C$_1$–C$_6$-alkyl, C$_3$–C$_6$-alkynyloxycarbonyl-C$_1$–C$_6$-alkyl, C$_3$–C$_6$-cycloalkoxy-C$_1$–C$_6$-alkyl, C$_3$–C$_6$-alkenyloxy-C$_1$–C$_6$-alkyl, C$_3$–C$_6$-alkynyloxy-C$_1$–C$_6$-alkyl, C$_1$–C$_6$-haloalkoxy-C$_1$–C$_6$-alkyl, C$_3$–C$_6$-haloalkenyloxy-C$_1$–C$_6$-alkyl, C$_3$–C$_6$-haloalkynyloxy-C$_1$–C$_6$-alkyl, C$_3$–C$_6$-cycloalkyl-C$_1$–C$_6$-thioalkyl, C$_3$–C$_6$-alkenylthio-C$_1$–C$_6$-alkyl, C$_3$–C$_6$-alkynylthio-C$_1$–C$_6$-alkyl, cyano-C$_1$–C$_6$-alkyl, C$_3$–C$_6$-halocyclo-C$_1$–C$_6$-alkyl, halo-C$_3$–C$_6$-alkenyl, C$_1$–C$_6$-alkoxy-C$_3$–C$_6$-alkenyl, C$_1$–C$_6$-haloalkoxy-C$_3$–C$_6$-alkenyl, C$_1$–C$_6$-alkylthio-C$_3$–C$_6$-alkenyl, C$_3$–C$_6$-haloalkynyl, C$_1$–C$_6$-alkoxy-C$_3$–C$_6$-alkynyl, C$_3$–C$_6$-haloalkoxyalkynyl, C$_1$–C$_6$-alkylthioalkynyl, C$_1$–C$_6$-alkylcarbonyl, CHR$^{16}$COR$^{17}$, CHR$^{16}$P(O) (OR$^{17}$)$_2$, P(O) (OR$^{17}$)$_2$, CHR$^{16}$P(S) (OR$^{17}$)$_2$, CHR$^{16}$C(O)NR$^{11}$R$^{12}$, CHR$^{16}$C(O)NH$_2$, C$_1$–C$_6$-alkyl, which is substituted by phenoxy or benzyloxy, where the rings for their part may be substituted by halogen, C$_1$–C$_4$-alkyl or C$_1$–C$_4$-haloalkyl, benzyl which may be substituted by halogen, C$_1$–C$_4$-alkyl or C$_1$–C$_4$-haloalkyl, or is phenyl or pyridyl which may be substituted by halogen, C$_1$–C$_4$-alkyl, C$_1$–C$_4$-haloalkyl or C$_1$–C$_4$-alkoxy;

m has the value 0, 1, 2 or 3;
n has the value 0, 1 or 2;
Q is one of the radicals Q-1 to Q-7

Q-1
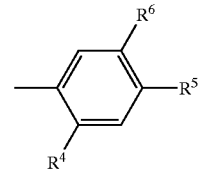

Q-2
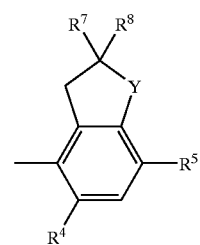

Q-3
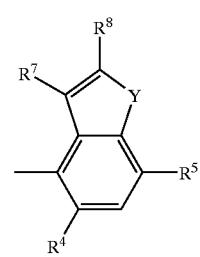

Q-4
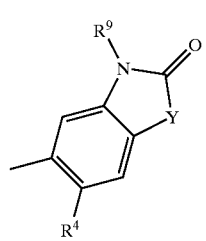

Q-5
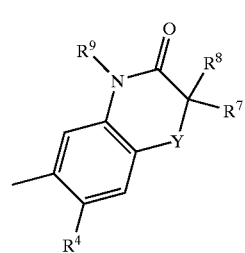

Q-6
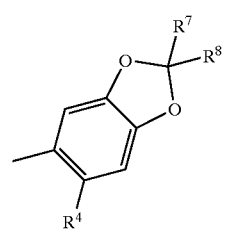

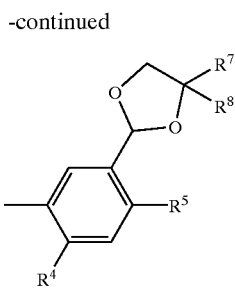

where
Y² is oxygen or sulfur;
R⁴ is hydrogen or halogen;
R⁵ is $C_1$–$C_6$-alkyl, $C_1$–$C_6$-haloalkyl, $OCH_3$, $OCHF_2$, halogen, CN or $NO_2$;
R⁶ is hydrogen, $C_1$–$C_6$-alkyl, $C_1$–$C_6$haloalkyl, halogen, $OR^{10}$, $S(O)_nR^{10}$, $COR^{10}$, $COOR^{10}$, $C(O)SR^{10}$, $SCH_2C\equiv CH$, $C(O)NR^{11}R^{12}$, CHO, $CH=CHCC-OR^{10}$, $CO-ON=CR^{13}R^{14}$, $NO_2$, CN, $NHCO_2R^{15}$, $NHSO_2NHR^{15}$, $-C(R^{18})=C(R^{19})-CO-R^{20}$, $-CH(R^{18})-CH(R^{19})-CO-R^{20}$, $-C(R^{18})=C(R^{19})-CO-N(R^{20}, R^{21})$, $-CH(R^{18})-CH(R^{19})-CO-N(R^{20}, R^{21})$, $-C(R^{21})=N-OR^{22}$, $-COOC(R^{23})(R^{24})-COOR^{25}$, $-CO-N(R^{26})-OR^{22}$ or $-C(OR^{27})=N-OR^{22}$;
R⁷, R⁸ independently of one another are hydrogen, $C_1$–$C_6$-alkyl, $C_1$–$C_6$-haloalkyl or halogen; if Q is Q-2, Q-5 or Q-6, R⁷ and R⁸ may, together with the linking carbon atom, form a group C=O;
R⁹ is $C_1$–$C_6$-alkyl, $C_1$–$C_6$-haloalkyl, $C_1$–$C_6$-alkoxy, $C_1$–$C_6$-alkoxy-$C_1$–$C_6$-alkyl, $C_2$–$C_6$-alkenyl or $C_2$–$C_6$-alkynyl;
R¹⁰ is one of the radicals indicated under R³;
R¹¹, R¹³ independently of one another are hydrogen or $C_1$–$C_6$-alkyl;
R¹², R¹⁴ independently of one another are $C_1$–$C_6$-alkyl or phenyl which may be substituted by halogen, $C_1$–$C_4$-alkyl, $C_1$–$C_4$-haloalkyl or $C_1$–$C_4$-alkoxy;
R¹¹, and R¹² together may be a group $-(CH_2)_5-$, $-(CH_2)_4-$ or $-CH_2CH_2OCH_2CH_2-$ where each ring may be substituted by $C_1$–$C_3$-alkyl, or may be phenyl or benzyl;
R¹³ and R¹⁴ together with the linking carbon atom may also form a $C_3$–$C_8$-cycloalkyl group;
R¹⁵ is $C_1$–$C_6$-alkyl or $C_1$–$C_6$-haloalkyl;
R¹⁶ is hydrogen or $C_1$–$C_6$-alkyl;
R¹⁷ is $C_1$–$C_6$-alkyl, $C_2$–$C_6$-alkenyl or $C_2$–$C_6$-alkynyl;
R¹⁸, R²³, R²⁴ are each hydrogen or $C_1$–$C_3$-alkyl;
R¹⁹ is halogen, cyano or methyl;
R²⁰ is hydroxyl, $C_1$–$C_6$-alkoxy, $C_3$–$C_6$-cycloalkoxy, $C_1$–$C_4$-alkoxy-$C_1$–$C_4$-alkoxy, $C_1$–$C_4$-alkylthio-$C_1$–$C_4$-alkoxy, $C_1$–$C_4$-alkylsulfinyl-$C_1$–$C_4$-alkoxy, $C_1$–$C_4$-alkylsulfonyl-$C_1$–$C_4$-alkoxy, cyano-$C_1$–$C_6$-alkoxy, $C_1$–$C_4$-alkoxycarbonyl-$C_1$–$C_4$-alkoxy, $C_3$–$C_6$-alkenyloxy, $C_3$–$C_6$-alkynyloxy, partially or fully halogenated $C_1$–$C_6$-alkoxy, partially or fully halogenated $C_3$–$C_6$-alkenyloxy, partially or fully halogenated $C_3$–$C_6$-alkynyloxy, $C_1$–$C_6$-alkylthio, furthermore $C_1$–$C_6$-alkoxy which may carry two additional $C_1$–$C_6$-alkoxy substituents,
R²¹ is hydrogen, $C_1$–$C_6$-alkyl or $C_1$–$C_6$-haloalkyl;
R²² is hydrogen, $C_1$–$C_6$-alkyl, $C_1$–$C_4$-alkoxy-$C_1$–$C_4$-alkyl, $C_1$–$C_6$-haloalkyl, $C_1$$C_6$-cyanoalkyl, $C_3$-$C_6$-cycloalkyl, $C_3$–$C_6$-alkenyl, $C_3$–$C_6$-alkynyl, $C_3$–$C_6$-haloalkenyl, $C_3$–$C_6$-haloalkynyl, carboxyl-$C_1$–$C_6$-alkyl, $C_1$–$C_6$-alkoxycarbonyl-$C_1$–$C_4$-alkyl, $C_1$–$C_6$-alkylcarbonyl-$C_1$–$C_6$-alkyl or $C_1$–$C_6$-alkylcarbonyloxy-$C_1$–$C_6$-alkyl;
R²⁵ is hydrogen, $C_1$–$C_6$-alkyl, $C_3$–$C_6$-cycloalkyl, $C_1$–$C_6$-alkoxy-$C_1$–$C_4$-alkyl, cyano-$C_1$–$C_6$-alkyl, halo-$C_1$–$C_6$-alkyl, $C_3$–$C_6$-alkenyl or $C_3$–$C_6$-alkynyl;
R²⁶, R²⁷ independently of one another are $C_1$–$C_6$-alkyl, $C_1$–$C_4$-alkoxy-$C_1$–$C_4$-alkyl, $C_3$–$C_6$-cycloalkyl, $C_3$–$C_6$-alkenyl, $C_3$–$C_6$-alkynyl, $C_1$–$C_6$-haloalkyl, $C_1$–$C_6$-cyanoalkyl, $C_3$–$C_6$-haloalkenyl, $C_3$–$C_6$-haloalkynyl or $C_1$–$C_6$-alkoxycarbonyl-$C_1$–$C_4$-alkyl;
R²⁶ is additionally hydrogen.

Additionally, the invention relates to novel fused triazoles of the formula I'

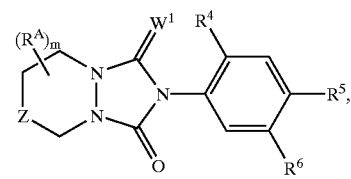

where Z is oxygen, sulfur, SO or $SO_2$, to their use in crop protection, and to fuse triazoles of the formula I".

Furthermore, the invention relates to substituted N-methyleneimino-N'-phenylureas of the formula III',

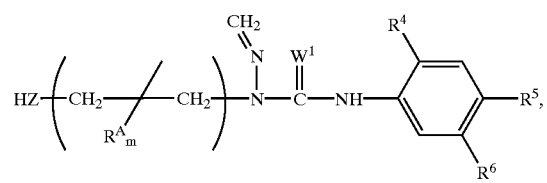

where:
Z is O, S, S=O or $SO_2$;
R^A is halogen or $C_1$–$C_3$-alkyl;
W¹ is oxygen or sulfur;
R⁴ is hydrogen or halogen;
R⁵ is halogen, cyano or trifluoromethyl;
R⁶ is a group $-C(R^{18})=C(R^{19})-CO-R^{20}$, $-CH(R^{18})-CH(R^{19})-CO-R^{20}$, $-C(R^{18})=C(R^{19})-CO-N(R^{20},R^{21})$ $-CH(R^{18})-CH(R^{19})-CO-N(R^{20}, R^{21})$, $-C(R^{21})=N-OR^{22}$, $-CO-OC(R^{23})(R^{24})-CO-OR^{25}$, $CO-N(R^{26})-OR^{22}$ or $-C(OR^{27})=N-OR^{22}$;
R¹⁸, R²³,
R²⁴ are each hydrogen or $C_1$–$C_3$-alkyl;
R¹⁹ is halogen, cyano or methyl;
R²⁰ is hydroxyl, $C_1$–$C_6$-alkoxy, $C_3$–$C_6$-cycloalkoxy, $C_1$–$C_4$-alkoxy-$C_1$–$C_4$-alkoxy, $C_1$–$C_4$-alkylthio-$C_1$–$C_4$-alkoxy, $C_1$–$C_4$-alkylsulfinyl-$C_1$–$C_4$-alkoxy, $C_1$–$C_4$-alkylsulfonyl-$C_1$–$C_4$-alkoxy, cyano-$C_1$–$C_6$-alkoxy, $C_1$–$C_4$-alkoxycarbonyl-$C_1$–$C_4$-alkoxy, $C_3$–$C_6$-alkenyloxy, $C_3$–$C_6$-alkynyloxy, partially or fully halogenated $C_1$–$C_6$-alkoxy, partially or fully halogenated $C_3$–$C_6$-alkenyloxy, partially or fully halogenated $C_3$–$C_6$-alkynyloxy, $C_1$–$C_6$-alkylthio, furthermore $C_1$–$C_6$-alkoxy which may carry two additional $C_1$–$C_6$-alkoxy substituents;

$R^{21}$ is hydrogen, $C_1-C_6$-alkyl or $C_1-C_6$-haloalkyl;

$R^{22}$ is hydrogen, $C_1-C_6$-alkyl, $C_1-C_4$-alkoxy-$C_1-C_4$-alkyl, $C_1-C_6$-haloalkyl, $C_1-C_6$-cyanoalkyl, $C_3-C_6$-cycloalkyl, $C_3-C_6$-alkenyl, $C_3-C_6$-alkynyl, $C_3-C_6$-haloalkenyl, $C_3-C_6$-haloalkynyl, carboxyl-$C_1-C_6$-alkyl, $C_1-C_6$-alkoxycarbonyl-$C_1-C_4$-alkyl, $C_1-C_6$-alkylcarbonyl-$C_1-C_6$-alkyl or $C_1-C_6$-alkylcarbonyloxy-$C_1-C_6$-alkyl;

$R^{25}$ is hydrogen, $C_1-C_6$-alkyl, $C_3-C_6$-cycloalkyl, $C_1-C_6$-alkoxy-$C_1-C_4$-alkyl, cyano-$C_1-C_6$-alkyl, halo-$C_1-C_6$-alkyl, $C_3-C_6$-alkenyl or $C_3-C_6$-alkynyl;

$R^{26}$, $R^{27}$ are $C_1-C_6$-alkyl, $C_1-C_4$-alkoxy-$C_1-C_4$-alkyl, $C_3-C_6$-cycloalkyl, $C_3-C_6$-alkenyl, $C_3-C_6$-alkynyl, $C_1-C_6$-haloalkyl, $C_1-C_6$-cyanoalkyl, $C_3-C_6$-haloalkenyl, $C_3-C_6$-haloalkynyl or $C_1-C_6$-alkoxycarbonyl-$C_1-C_4$-alkyl, and $R^{26}$ is additionally hydrogen;

m is 0, 1, 2 or 3, and to their use for preparing fused triazoles of the formula I'.

EP A 210 137 and WO 94/10173 described herbicidally active fused triazoles and processes for their preparation. According to the process described in WO 94/10173, N'-substituted N-aminourea derivatives of the formula II are reacted with aldehydes in the presence of acid to give substituted tetrahydro-4H-1,3,4-oxa(or thia)diazines of the formula IV, and the latter are cyclized with phosgene or a phosgene substitute to the compounds of the formula I.

However, this process affords fused triazoles only in the case of monosubstitution by phenyl, and not in the desired yields.

It is an object of the present invention to provide an improved process for preparing the fused triazoles described in WO 94/10173, in particular for products which are polysubstituted by phenyl.

We have found that this object is achieved and that fused triazoles of the formula I can be obtained in high yield and improved purity by reacting, in a first step, N'-substituted N-aminourea derivatives II

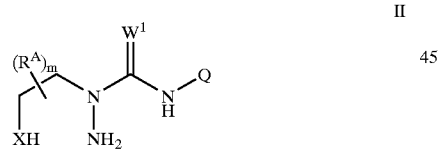

with aqueous formaldehyde or paraformaldehyde in the absence of acid in neutral or weakly alkaline medium to give novel N-methyleneimino-N'-substituted ureas of the formula III

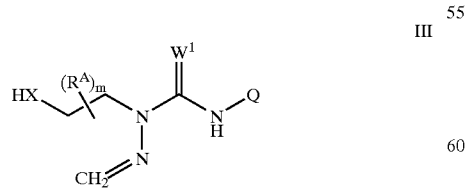

cyclizing these in a second step in the presence of catalytical amounts of acid or a neutral or acidic surface-active metal oxide to substituted tetrahydro-4H-1,3,4-oxa(or thia) diazines of the formula IV

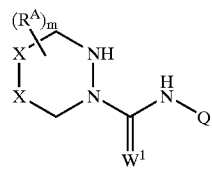

and cyclizing the latter with phosgene or a phosgene substitute to give the compounds of the formula I.

The terms used in the definition of the substituents are collective terms for individual listings of the individual group members. All alkyl radicals can be straight-chain or branched.

The haloalkyl radical preferably carries one to five identical or different halogen atoms.

Examples of specific meanings are:

halogen: fluorine, chlorine, bromine or iodine, preferably fluorine or chlorine;

$C_1-C_3$-alkyl: methyl, ethyl, n-propyl or 1-methylethyl;

$C_1-C_4$-alkyl: $C_1-C_3$-alkyl as mentioned above, and also n-butyl, 1-methylpropyl, 2-methylpropyl or 1,1-dimethylethyl;

$C_1-C_6$-alkyl: $C_1-C_4$-alkyl as mentioned above, and also n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl;

$(C_1-C_6$-alkyl)carbonyl: methylcarbonyl, ethylcarbonyl, n-propylcarbonyl, 1-methylethylcarbonyl, n-butylcarbonyl, 1-methylpropylcarbonyl, 2-methylpropylcarbonyl, 1,1-dimethylethylcarbonyl, n-pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, n-hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl, in particular methylcarbonyl, ethylcarbonyl or 1-methylethylcarbonyl;

$C_3-C_4$-alkenyl: prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl or 2-methylprop-2-en-1-yl;

$C_3-C_6$-alkenyl: $C_3-C_4$-alkenyl as mentioned above, and also n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1- yl, 1-ethylprop-1-en-2-yl, 1-ethylprop-2-en-1-yl, n-hex-1-en-2-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl, preferably ethenyl or prop-2-en-1-yl;

$C_3$–$C_4$-alkynyl: prop-1-in-1-yl, prop-2-in-3-yl, n-but-1-in-1-yl, n-but-1-in-4-yl or n-but-2-in-1-yl;

$C_3$–$C_6$-alkynyl: $C_3$–$C_4$-alkynyl as mentioned above, and also, for example, n-pent-1-in-1-yl, n-pent-1-in-3-yl, n-pent-1-in-4-yl, n-pent-1-in-5-yl, n-pent-2-in-1-yl, n-pent-2-in-4-yl, n-pent-2-in-5-yl, 3-methylbut-1-in-1-yl, 3-methylbut-1-in-3-yl, 3-methylbut-1-in-4-yl, n-hex-1-in-1-yl, n-hex-1-in-3-yl, n-hex-1-in-4-yl, n-hex-1-in-5-yl, n-hex-1-in-6-yl, n-hex-2-in-1-yl, n-hex-2-in-4-yl, n-hex-2-in-5-yl, n-hex-2-in-6-yl, n-hex-3-in-1-yl, n-hex-3-in-2-yl, 3-methylpent-1-in-1-yl, 3-methylpent-1-in-3-yl, 3-methylpent-1-in-4-yl, 3-methylpent-1-in-5-yl, 4-methylpent-1-in-1-yl, 4-methylpent-2-in-4-yl or 4-methylpent-2-in-5-yl, in particular prop-2-in-1-yl or 1-methylprop-2-in-1-yl;

—$C_3$–$C_6$-cycloalkyl-$C_1$–$C_4$-alkyl: cyclopropylmethyl, cyclobutylmethyl, cyclopentylmethyl, cyclohexylmethyl, cycloheptylmethyl, cyclooctylmethyl, 1-(cyclopropyl)ethyl, 1-(cyclobutyl)ethyl, 1-(cyclopentyl)ethyl, 1-(cyclohexyl)ethyl, 2-(cyclopropyl)ethyl, 2-(cyclobutyl)ethyl, 2-(cyclopentyl)ethyl, 2-(cyclohexyl)ethyl, 2-(cyclopropyl)ethyl, 3-(cyclopropyl)ethyl, 3-(cyclopropyl)propyl, 3-(cyclobutyl)propyl, 3-(cyclopentyl)propyl, 3-(cyclohexyl)propyl, 4-(cyclopropyl)butyl, 4-(cyclobutyl)butyl, 4-(cyclopentyl)butyl, 4-(cyclohexyl)butyl, in particular cyclopentylmethyl or cyclohexylmethyl;

$C_3$–$C_6$-cycloalkyl-$C_1$–$C_6$-alkyl: cyclopropylmethyl, cyclobutylmethyl, cyclopentylmethyl, cyclohexylmethyl, cycloheptylmethyl, cyclooctylmethyl, 1-(cyclopropyl)ethyl, 1-(cyclobutyl)ethyl, 1-(cyclopentyl)ethyl, 1-(cyclohexyl)ethyl, 2-(cyclopropyl)ethyl, 2-(cyclobutyl)ethyl, 2-(cyclopentyl)ethyl, 2-(cyclohexyl)ethyl, 2-(cyclopropyl)propyl, 3-(cyclopropyl)propyl, 3-(cyclobutyl)propyl, 3-(cyclopentyl)propyl, 3-(cyclohexyl)propyl, 2-(cyclopropyl)butyl, 3-(cyclopropyl)butyl, 4-(cyclopropyl)butyl, 4-(cyclobutyl)butyl, 4-(cyclopentyl)butyl, 4-(cyclohexyl)butyl, 2-(cyclopropyl)pentyl, 3-(cyclopropyl)pentyl, 4-(cyclopropyl)pentyl, 5-(cyclopropyl)pentyl, 2-(cyclobutyl)pentyl, 3-(cyclobutyl)pentyl, 5-(cyclobutyl)pentyl, 2-(cyclopropyl)hexyl, 3-(cyclopropyl)hexyl, 6-(cyclopropyl)hexyl, in particular cyclopentylmethyl or cyclohexylmethyl;

$C_3$–$C_6$-cycloalkoxy: cyclopropoxy, cyclobutoxy, cyclopentoxy or cyclohexoxy;

$C_1$–$C_4$-alkoxy: $OCH_3$, $OC_2H_5$, $OCH_2$—$C_2H_5$, $OCH(CH_3)_2$, n-butoxy, 1-methylpropoxy, 2-methylpropoxy or $OC(CH_3)_3$, in particular $OCH_3$ or $OC_2H_5$;

$C_1$–$C_6$-alkoxy: $C_1$–$C_4$-alkoxy as mentioned above, and also, for example, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, in particular $OCH_3$, $OC_2H_5$ or $OCH(CH_3)_2$;

($C_1$–$C_6$-alkoxy)carbonyl: ($C_1$–$C_4$-alkoxy)carbonyl as mentioned above, and also, for example, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, in particular methoxycarbonyl, ethoxycarbonyl or 1-methylethoxycarbonyl;

Cyano-$C_1$–$C_6$-alkyl is, for example, $CH_2CN$, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl or 2-cyanomethylprop-2-yl, in particular $CH_2CN$ or 2-cyanoethyl;

Cyano-$C_1$–$C_6$-alkoxy: 1-cyano-1-ethoxy, 2-cyano-1-ethoxy, 1-cyano-1-propoxy, 2-cyano-1-propoxy, 3-cyano-1-propoxy, 1-cyano-2-propoxy, 1-cyano-1-butoxy, 2-cyano-1-butoxy, 3-cyano-1-butoxy, 4-cyano-1-butoxy, 1-cyano-2-butoxy, 2-cyano-2-butoxy, 1-cyano-3-butoxy, 2-cyano-3-butoxy, 1-cyano-2-methyl-3-propoxy, 2-cyano-2-methyl-3-propoxy, 3-cyano-2-methyl-3-propoxy or 2-cyanomethyl-2-propoxy in particular 2-cyano-1-ethoxy or 3-cyano-1-propoxy;

$C_1$–$C_6$-Haloalkyl: $C_1$–$C_4$-alkyl as mentioned above which is partially or fully substituted by fluorine, chlorine and/or bromine,. i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-chloroethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 1-chloro-1,2,2-trifluoroethyl, 2,2-dichloro-2-fluoroethyl, 1,2,2-trifluoroethyl, 2,2,2-trichloroethyl, pentafluoroethyl or 3-chloropropyl, preferably trifluoromethyl;

$C_3$–$C_6$-Haloalkenyl: $C_3$–$C_6$-alkenyl as mentioned above which is partially or fully substituted by fluorine, chlorine and/or bromine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl, in particular 2-chloroallyl or 3,3-dichloroallyl;

$C_3$–$C_6$-Haloalkynyl: $C_3$–$C_6$-alkynyl as mentioned above which is partially or fully substituted by fluorine, chlorine and/or bromine, i.e., for example, 3-chloropropargyl, 3-bromopropargyl, 3-fluoropropargyl, 3,3,3-trifluoropropargyl, 4-chloro-but-2-inyl, 4-bromo-but-2-inyl, 4,4,4-trifluoro-but-2-inyl, 1,4-dichloro-but-2-inyl, 5-chloro-pent-3-inyl, 5-fluoropent-3-inyl, 5,5,5-trifluoropent-3-inyl, 6-chlorohex-2-inyl, preferably 3-chloropropargyl, 3,3,3-trifluoropropargyl, 4,4,4-trifluorobut-2-inyl;

$C_1$–$C_4$-Haloalkoxy: a $C_1$–$C_4$-alkoxy radical as mentioned above which is partially or fully substituted by fluorine, chlorine, bromine and/or iodine, i.e., for example, $OCH_2F$, $OCHF_2$, $OCF_3$, $OCH_2Cl$, $OCH(Cl)_2$, $OC(Cl)_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$–$C_2F_5$, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy, in particular 2-chloroethoxy or 2,2,2-trifluoroethoxy;

$C_1$–$C_6$-Haloalkoxy: a $C_1$–$C_6$-alkoxy radical as mentioned above which is partially or fully substituted by fluorine, chlorine, bromine and/or iodine, i.e., for example, one of the radicals mentioned under $C_1$–$C_4$-haloalkoxy or 5-fluoro-1-pentoxy, 5-chloro-1-pentoxy, 5-bromo-1-pentoxy, 5-iodo-1-pentoxy, 5,5,5-trichloro-1-pentoxy, undecafluoropentoxy, 6-fluoro-1-hexoxy, 6-chloro-1-hexoxy, 6-bromo-1-hexoxy, 6-iodo-1-hexoxy, 6,6,6-trichloro-1-hexoxy or dodecafluorohexoxy, in particular $OCH_2F$, $OCHF_2$, $OCF_3$, $OCH_2Cl$, 2-fluoroethoxy, 2-chloroethoxy or 2,2,2-trifluoroethoxy;

$C_3$–$C_6$-Alkenyloxy: prop-1-en-1-yloxy, prop-2-en-1-yloxy, 1-methylethenyloxy, n-buten-1-yloxy, n-buten-2-yloxy, n-buten-3-yloxy, 1-methylprop-1-en-1-yloxy, 2-methylprop-1-en-1-yloxy, 1-methylprop-2-en-1-yloxy, 2-methylprop-2-en-1-yloxy, n-penten-1-yloxy, n-penten-2-yloxy, n-penten-3-yloxy, n-penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-b-en-1-yloxy, 1,2-diethylprop-2-en-1-yloxy, 1-ethylprop-1-en-2-yloxy, 1-ethylprop-2-en-1- yloxy, n-hex-1-en-1-yloxy, n-hex-2-en-1-yloxy, n-hex-3-en-1-yloxy, n-hex-4-en-1-yloxy, n-hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy or 1-ethyl-2-methylprop-2-en-1-yloxy, preferably ethenyloxy or prop-2-en-1-yloxy;

$C_3$–$C_6$-Alkynyloxy: propargyloxy, prop-1-in-1-oxy, but-1-in-3-oxy, 3-methylbut-1-in-3-oxy, 3,3-dimethylbut-1-in-4-oxy, pent-1-in-3-oxy, 3-methylpent-1-in-3-oxy, hex-3-in-5-oxy, in particular propargyloxy, but-1-in-3-oxy or 3-methylbut-1-in-3-oxy;

$C_1$–$C_6$-Alkylthio-$C_1$–$C_6$-alkoxy: $C_1$–$C_6$-alkoxy which is substituted by $C_1$–$C_6$-alkylthio as mentioned above, i.e., for example methylthiomethoxy, ethylthiomethoxy, n-propylthiomethoxy, (1-methylethylthio)methoxy, n-butylthiomethoxy, (1-methylpropylthio)methoxy, (2-methylpropylthio)methoxy, (1,1-dimethylethylthio)methoxy, 2-(methylthio)ethoxy, 2-(ethylthio)ethoxy, 2-(n-propylthio)ethoxy, 2-(1-methylethylthio)ethoxy, 2-(n-butylthio)ethoxy, 2-(1-methylpropylthio)ethoxy, 2-(2-methylpropylthio)ethoxy, 2-(1,1-dimethylethylthio)ethoxy, 2-(methylthio)propoxy, 2-(ethylthio)propoxy, 2-(n-propylthio)propoxy, 2-(1-methylethylthio)propoxy, 2-(n-butylthio)propoxy, 2-(1-methylpropylthio)propoxy, 2-(2-methylpropylthio)propoxy, 2-(1,1-dimethylethylthio)propoxy, 3-(methylthio)propoxy, 3-(ethylthio)propoxy, 3-(n-propylthio)propoxy, 3-(1-methylethylthio)propoxy, 3-(n-butylthio)propoxy, 3-(1-methylpropylthio)propoxy, 3-(2-methylpropylthio)propoxy, 3-(1,1-dimethylethylthio)propoxy, 2-(methylthio)butoxy, 2-(ethylthio)butoxy, 2-(n-propylthio)butoxy, 2-(1-methylethylthio)butoxy, 2-(n-butylthio)butoxy, 2-(1-methylpropylthio)butoxy, 2-(2-methylpropylthio)butoxy, 2-(1,1-dimethylethylthio)-butoxy, 3-(methylthio)butoxy, 3-(ethylthio)butoxy, 3-(n-propylthio)butoxy, 3-(1-methylethylthio)butoxy, 3-(n-butylthio)butoxy, 3-(1-methylpropylthio)butoxy, 3-(2-methylpropylthio)butoxy, 3-(1,1-dimethylethylthio) butoxy, 4-(methylthio)butoxy, 4-(ethylthio)butoxy, 4-(n-propylthio)butoxy, 4-(1-methylethylthio)butoxy, 4-(n-butylthio)butoxy, 4-(1-methylpropylthio)butoxy, 4-(2-methylpropylthio)butoxy, 4-(1,1-dimethylethylthio)butoxy, 5-(methylthio)pentoxy, 5-(ethylthio)pentoxy, 5-(n-propylthio)pentoxy, 5-(1-methylethylthio)pentoxy, 5-(n-butylthio)pentoxy, 5-(1-methylpropylthio)pentoxy, 5-(2-methylpropylthio)pentoxy, 5-(1,1-dimethylethylthio)pentoxy, 6-(methylthio)hexoxy, 6-(ethylthio)hexoxy, 6-(n-propylthio)hexoxy, 6-(1-methylethylthio)hexoxy, 6-(n-butylthio)hexoxy, 6-(1-methylpropylthio)hexoxy, 6-(2-methylpropylthio)hexoxy or 6-(1,1-dimethylethylthio) hexoxy, in particular methylthiomethoxy or ethylthioethoxy;

$C_1$–$C_6$-Alkylthio: $SCH_3$, $SC_2H_5$, $SCH_2$—$C_2H_5$, $SCH(CH_3)_2$, n-butylthio, $SCH(CH_3)$—$C_2H_5$, 2-methylpropylthio, 1,1-dimethylethylthio, n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, in particular $SCE_3$ or $SC_2H_5$;

$C_1$–$C_6$-Alkylthio-$C_1$–$C_6$-alkyl: $C_1$–$C_6$-alkyl which is substituted by $C_1$–$C_6$-alkylthio as mentioned above, i.e., for example, methylthiomethyl, ethylthiomethyl, n-propylthiomethyl, (1-methylethylthio)methyl, n-butylthiomethyl, (1-methyl-propylthio)methyl, (2-methylpropylthio)methyl, (1,1-dimethylethylthio)methyl, 2-methylthioethyl, 2-ethylthioethyl, 2-(n-propylthio)ethyl, 2-(1-methylethylthio)ethyl, 2-(n-butylthio)ethyl, 2-(1-methylpropylthio)ethyl, 2-(2-methylpropylthio)ethyl, 2-(1,1-dimethylethylthio)ethyl, 2-(methylthio)propyl, 3-(methylthio)propyl, 2-(ethylthio)-propyl, 3-(ethylthio)propyl, 3-(propylthio)propyl, 3-(butylthio)propyl, 4-(methylthio)butyl, 4-(ethylthio)butyl, 4-(n-propylthio)butyl or 4-(n-butylthio)butyl, in particular 2-(methylthio)ethyl;

$C_1$–$C_4$-Alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl or 1,1-dimethylethylsulfonyl, in particular methylsulfonyl or ethylsulfonyl;

$C_1$–$C_6$-Alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl, 1,1-dimethylethylsulfonyl, n-pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, n-hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl, in particular methylsulfonyl;

$C_1$–$C_4$-Alkylsulfinyl: methylsulfinyl, ethylsulfinyl, n-propylsulfinyl, 1-methylethylsulfinyl, n-butylsulfinyl, 1-methylpropylsulfinyl, 2-methylpropylsulfinyl or 1,1-dimethylethylsulfinyl, in particular methylsulfinyl or ethylsulfinyl;

$C_1$–$C_6$-Alkylsulfinyl: methylsulfinyl, ethylsulfinyl, n-propylsulfinyl, 1-methylethylsulfinyl, n-butylsulfinyl, 1-methylpropylsulfinyl, 2-methylpropylsulfinyl, 1,1-dimethylethylsulfinyl, n-pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, n-hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl, in particular methylsulfinyl;

$C_1$–$C_4$-Alkokxy-$C_1$–$C_4$-alkyl: $C_1$–$C_4$-alkyl which is substituted by $C_1$–$C_4$-alkoxy such as methoxy, ethoxy, n-propoxy, 1-methylethoxy, n-butoxy, 1-methylpropoxy, 2-methylpropoxy and 1,1-dimethylethoxy, i.e., for example, $CH_2OCH_3$, $CH_2OC_2H_5$, n-propoxymethyl, (1-methylethoxy)methyl, n-butoxymethyl, (1-methylpropoxy)methyl, (2-methylpropoxy)methyl, (1,1-dimethylethoxy)methyl, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably n-propoxymethyl, (1-methylethoxy)methyl, 2-(n-propoxy)ethyl or 2-(1-methylethoxy)ethyl, and particularly preferably $CH_2OCH_3$, $CH_2OC_2H_5$, 2-methoxyethyl or 2-ethoxyethyl;

$C_1$–$C_6$-Alkokxy-$C_1$–$C_6$-alkyl: $C_1$–$C_6$-alkyl which is substituted by $C_1$–$C_6$-alkoxy as mentioned above, i.e., for example, methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy) methyl, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)

ethyl, 2-(1,1-dimethylethoxy)ethyl, 2-(methoxy) propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, in particular methoxymethyl or 2-methoxyethyl;

$C_1$–$C_4$-alkoxy-$C_1$–$C_4$-alkoxy: $C_1$–$C_4$-alkoxy which is substituted by $C_1$–$C_4$-alkoxy such as methoxy, ethoxy, n-propoxy, 1-methylethoxy, n-butoxy, 1-methylpropoxy, 2-methylpropoxy and 1,1-dimethylethoxy, i.e., for example, $OCH_2OCH_3$, $OCH_2OC_2H_5$, n-propoxymethoxy, (1-methylethoxy)methoxy, n-butoxymethoxy, (1-methylpropoxy)methoxy, (2-methylpropoxy)methoxy, (1,1-dimethylethoxy)methoxy, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(n-propoxy)propoxy, 2-(1-methylethoxy)propoxy, 2-(n-butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(n-propoxy)propoxy, 3-(1-methylethoxy)propoxy, 3-(n-butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(n-propoxy)butoxy, 2-(1-methylethoxy)butoxy, 2-(n-butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(n-propoxy)butoxy, 3-(1-methylethoxy)-butoxy, 3-(n-butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(n-propoxy)butoxy, 4-(1-methylethoxy)butoxy, 4-(n-butoxy)butoxy, 4-(1-methylpropoxy)butoxy, 4-(2-methylpropoxy)butoxy or 4-(1,1-dimethylethoxy)butoxy, preferably n-propoxymethoxy, (1-methylethoxy)methoxy, 2-(n-propoxy)ethoxy or 2-(1-methylethoxy)ethoxy, and particularly preferably $OCH_2OCH_3$, $OCH_2OC_2H_5$, 2-methoxyethoxy or 2-ethoxyethoxy;

$C_1$–$C_6$-Alkokxy-$C_1$–$C_6$-alkoxy: $C_1$–$C_6$-alkoxy which is substituted by $C_1$–$C_6$-alkoxy as mentioned above, i.e., for example, methoxymethoxy, ethoxymethoxy, n-propoxymethoxy, (1-methylethoxy)methoxy, n-butoxymethoxy, (1-methylpropoxy)methoxy, (2-methylpropoxy)methoxy, (1,1-dimethylethoxy)methoxy, 2-(methoxy)ethoxy, 2-(ethoxy)ethoxy, 2-(n-propoxy)ethoxy, 2-(1-methylethoxy)ethoxy, 2-(n-butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(n-propoxy)propoxy, 2-(1-methylethoxy)propoxy, 2-(n-butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(n-propoxy)propoxy, 3-(1-methylethoxy)propoxy, 3-(n-butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(n-propoxy)butoxy, 2-(1-methylethoxy)butoxy, 2-(n-butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(n-propoxy)butoxy, 3-(1-methylethoxy)butoxy, 3-(n-butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(n-propoxy)butoxy, 4-(1-methylethoxy)butoxy, 4-(n-butoxy)butoxy, 4-(1-methylpropoxy)butoxy, 4-(2-methylpropoxy)butoxy, 4-(1,1-dimethylethoxy)butoxy, 5-(methoxy)pentoxy, 5-(ethoxy)pentoxy, 5-(n-propoxy)pentoxy, 5-(1-methylethoxy)pentoxy, 5-(n-butoxy)pentoxy, 5-(1-methylpropoxy)pentoxy, 5-(2-methylpropoxy)pentoxy, 5-(1,1-dimethylethoxy)pentoxy, 6-(methoxy)hexoxy, 6-(ethoxy)hexoxy, 6-(n-propoxy)hexoxy, 6-(1-methylethoxy)hexoxy, 6-(n-butoxy)hexoxy, 6-(1-methylpropoxy)hexoxy, 6-(2-methylpropoxy)hexoxy or 6-(1,1-dimethylethoxy)hexoxy, in particular methoxymethoxy or ethoxymethoxy;

Carboxy—$C_1$–$C_6$-alkyl: $C_1$–$C_6$-alkyl as mentioned above which is substituted by carboxyl, i.e., for example, carboxymethyl, 2-carboxy-1-ethyl, 3-carboxy-1-propyl, 1-carboxy-1-ethyl, 1-carboxy-1-propyl, 3-carboxy-2-propyl, 2-carboxy-2-propyl, 1-carboxy-1-butyl, 1-carboxy-2-butyl, 2-carboxy-2-butyl, 4-carboxy-1-butyl, 4-carboxy-2-butyl, 5-carboxy-1-pentyl, 5-carboxy-2-pentyl, 5-carboxy-3-pentyl, 5-carboxy-1-hexyl, in particular carboxymethyl, 2-carboxy-1-ethyl or 1-carboxy-1-ethyl;

($C_1$–$C_6$-Alkoxy)carbonyl-$C_1$–$C_2$-alkyl: $C_1$–$C_2$-alkyl which is substituted by ($C_1$–$C_6$-alkoxy)carbonyl such as $COOCH_3$, $COOC_2H_5$, n-propoxycarbonyl, $COOCH(CH_3)_2$, n-butoxycarbonyl, 1-methylpropoxycarbonyl, 2-methylpropoxycarbonyl, $COOC(CH_3)3$, n-pentoxycarbonyl, 1-methylbutoxycarbonyl and n-hexoxycarbonyl, i.e., for example, $CH_2$—$COOH_3$, $CH_2$—$COO_2H_5$, n-propoxycarbonylmethyl, $CH_2$—$COOH$ $(CH_3)_2$, n-butoxycarbonylmethyl, (1-methylpropoxycarbonyl)methyl, (2-methylpropoxycarbonyl)methyl, $CH_2$—$COOC(CH_3)_3$, n-pentoxycarbonylmethyl, (1-methylbutoxycarbonyl)methyl, n-hexoxycarbonylmethyl, 1-(methoxycarbonyl)ethyl, 1-(ethoxycarbonyl)ethyl, 1-(n-propoxycarbonyl)ethyl, 1-(1-methylethoxycarbonyl)ethyl, 1-(n-butoxycarbonyl)ethyl, 1-(n-pentoxycarbonyl)ethyl, 1-(1-methylbutoxycarbonyl)ethyl, 1-(n-hexoxycarbonyl)ethyl, 2-(methoxycarbonyl)ethyl, 2-(ethoxycarbonyl)ethyl, 2-(n-propoxycarbonyl)ethyl, 2-(1-methylethoxycarbonyl)ethyl, 2-(n-butoxycarbonyl)ethyl, 2-(1-methylpropoxycarbonyl)ethyl, 2-(2-methylpropoxycarbonyl)ethyl, 2-(1,1-dimethylethoxycarbonyl)ethyl;

($C_1$–$C_6$-Alkoxy) carbonyl-$C_1$–$C_4$-alkyl: ($C_1$–$C_6$-alkoxy)carbonyl-$C_1$–$C_2$-alkyl as mentioned above, and also 2-(methoxycarbonyl)propyl, 2-(ethoxycarbonyl) propyl, 2-(n-propoxycarbonyl)propyl, 2-(1-methylethoxycarbonyl)propyl, 2-(n-butoxycarbonyl) propyl, 2-(1-methylpropoxycarbonyl)propyl, 2-(2-methylpropoxycarbonyl)propyl, 2-(1,1-dimethylethoxycarbonyl)propyl, 3-(methoxycarbonyl) propyl, 3-(ethoxycarbonyl)propyl, 3-(n-propoxycarbonyl)propyl, 3-(1-methylethoxycarbonyl) propyl, 3-(n-butoxycarbonyl)propyl, 3-(1-methylpropoxycarbonyl)propyl, 3-(2-methylpropoxycarbonyl)propyl, 3-(1,1-dimethylethoxycarbonyl)propyl, 2-(methoxycarbonyl) butyl, 2-(ethoxycarbonyl)butyl, 2-(n-propoxycarbonyl) butyl, 2-(1-methylethoxycarbonyl)butyl, 2-(n-butoxycarbonyl)butyl, 2-(1-methylpropoxycarbonyl) butyl, 2-(2-methylpropoxycarbonyl)butyl, 2-(1,1-dimethylethoxycarbonyl)butyl, 3-(methoxycarbonyl) butyl, 3-(ethoxycarbonyl)butyl, 3-(n-propoxycarbonyl) butyl, 3-(1-methylethoxycarbonyl)butyl, 3-(n-butoxycarbonyl)butyl, 3-(1-methylpropoxycarbonyl) butyl, 3-(2-methylpropoxycarbonyl)butyl, 3-(1,1-dimethylethoxycarbonyl)butyl, 4-(methoxycarbonyl) butyl, 4-(ethoxycarbonyl)butyl, 4-(n-propoxycarbonyl) butyl, 4-(1-methylethoxycarbonyl)butyl, 4-(n-butoxycarbonyl)butyl, 4-(1-methylpropoxycarbonyl) butyl, 4-(2-methylpropoxycarbonyl)butyl or 4-(1,1-dimethylethoxycarbonyl)butyl, preferably $CH_2$—$COOH_3$, $CH_2$—$COO_2H_5$, 1-(methoxycarbonyl)ethyl, 2-methoxycarbonyl)ethyl or 1-(ethoxycarbonyl)ethyl;

($C_1$–$C_6$-Alkoxy)carbonyl-$C_1$–$C_6$-alkyl: $C_1$–$C_6$-alkyl which is substituted by ($C_1$–$C_6$-alkoxy)carbonyl as mentioned above, i.e., for example, methoxycarbonylmethyl, ethoxycarbonylmethyl, 1-(methoxycarbonyl)ethyl, 2-(methoxycarbonyl)ethyl, 2-(ethoxycarbonyl)ethyl, 3-(methoxycarbonyl)propyl, 4-(methoxycarbonyl)butyl, 5-(methoxycarbonyl)pentyl or 6-(methoxycarbonyl)hexyl;

($C_1$–$C_6$-Alkoxy)carbonyl-$C_1$–$C_4$-alkoxy: $C_1$–$C_6$-alkoxy which is substituted by ($C_1$–$C_6$-alkoxy)carbonyl as mentioned above, i.e., for example, methoxycarbonylmethoxy, ethoxycarbonylmethoxy, n-propoxycarbonylmethoxy, n-butoxycarbonylmethoxy, 1-(methoxycarbonyl) ethoxy, 2-(methoxycarbonyl)ethoxy, 2-(ethoxycarbonyl)ethoxy, 2-(n-propoxycarbonyl) ethoxy, 2-(n-butoxycarbonyl)ethoxy, 3-(methoxycarbonyl)propoxy, 3-(ethoxycarbonyl) propoxy, 3-(n-propoxycarbonyl)propoxy, 3-(n-butoxycarbonyl)propoxy, 4-(methoxycarbonyl)butoxy, 4-(ethoxycarbonyl)butoxy, 4-(n-propoxycarbonyl) butoxy, 4-(n-butoxycarbonyl)butoxy, 1-(ethoxycarbonyl)ethoxy, 1-(propoxycarbonyl) ethoxy, 2-(methoxycarbonyl)-2-propoxy, 2-(ethoxycarbonyl)-2-propoxy, 2-methyl-2-(methoxycarbonyl)-2-propoxy, in particular methoxycarbonylmethoxy, 2-methoxycarbonylethoxy or 1-(methoxycarbonyl)ethoxy;

$C_3$–$C_6$-Alkenyloxy-$C_1$–$C_6$-alkyl: $C_1$–$C_6$-alkyl which is substituted by $C_3$–$C_6$-alkenyloxy as mentioned above, preferably by allyloxy, 2-methylprop-2-en-1-yloxy, but-1-en-3-yloxy, but-1-en-4-yloxy or but-2-en-1-yloxy i.e., for example, allyloxymethyl, 2-allyloxyethyl or but-1-en-4-yloxymethyl;

$C_3$–$C_6$-Alkynyloxy-$C_1$–$C_6$-alkyl: $C_1$–$C_6$-alkyl which is substituted by $C_3$–$C_6$-alkynyloxy as mentioned above, preferably by propargyloxy, but-1-in-3-yloxy, but-1-in-4-yloxy or but-2-in-1-yloxy, i.e., for example, propargyloxymethyl or 2-propargyloxyethyl;

$C_3$–$C_6$-Cycloalkoxy-$C_1$–$C_4$-alkyl: cyclopropyloxymethyl, cyclobutyloxymethyl, cyclopentyloxymethyl, cyclohexyloxymethyl, 1-(cyclopropyloxy)ethyl, 1-(cyclobutyloxy)ethyl, 1-(cyclopentyloxy)ethyl, 1-(cyclohexyloxy)ethyl, 2-(cyclopropyloxy)ethyl, 2-(cyclobutyloxy)ethyl, 2-(cyclopentyloxy)ethyl, 2-(cyclohexyloxy)ethyl, 3-(cyclopropyloxy)propyl, 3-(cyclobutyloxy)propyl, 3-(cyclopentyloxy)propyl, 3-(cyclohexyloxy)propyl, 4-(cyclopropyloxy)butyl, 4-(cyclobutyloxy)butyl, 4-(cyclopentyloxy)butyl or 4-(cyclohexyloxy)butyl, in particular cyclopentyloxymethyl, cyclohexyloxymethyl or 2-(cyclopentyloxy)ethyl.

The N'-substituted N-aminourea derivatives of the formula II used as starting materials in the process according to the invention and processes for their preparation are known per se and described in the literature, for example in Wo 94/10173, so that reference should be made to this corresponding literature for further details.

Hereinbelow, the reaction conditions and the practice of the process are described with reference to the preparation of the novel fused triazoles I'; however, the specifications can be transferred to the preparation of all compounds of the formula I as claimed in claim 1.

When using the process according to the invention to prepare the compounds I' according to the invention in good yields and high purity, the following scheme results:

In the first step, substituted N-amino-N'-phenylureas of the formula II'

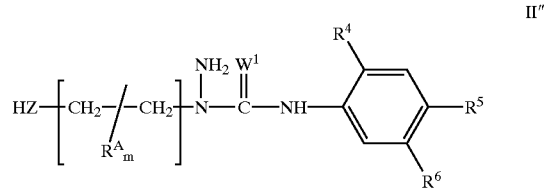

in which

Z=oxygen or sulfur, $R^A$, $W^1$, $R^4$, $R^5$ and $R^6$ are each as defined above and m=0, 1 or 2, are reacted with aqueous formaldehyde or paraformaldehyde in the absence of acid to give the novel N-methyleneimino-N'-phenylureas of the formula III'

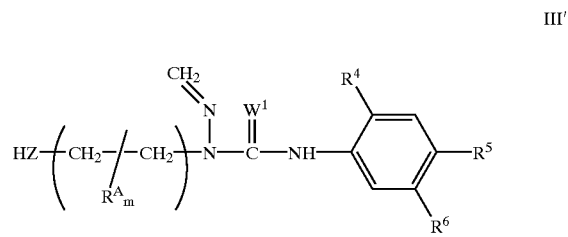

these are then cyclized in the presence of acid or a neutral or acidic surface-active metal oxide to the 4-(phenylcarbamoyl)tetrahydro-4H-1,3,4-oxa(or thia) diazines of the formula IV'

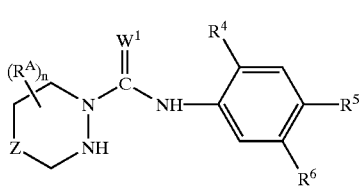

and the latter are cyclized using phosgene or a phosgene substitute to give the compounds of the formula I'.

If an N-amino-N-2-hydroxyethyl-N'-phenyl-substituted urea and aqueous formaldehyde are used, the process according to the invention can be represented by the following equation:

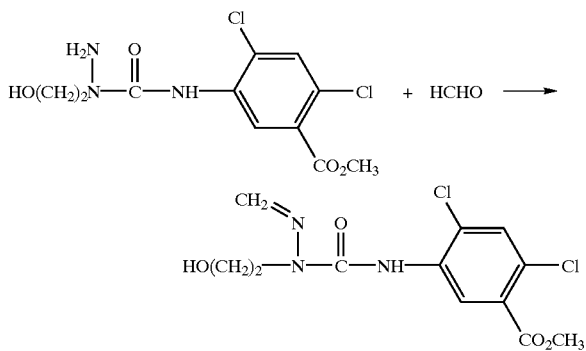

The subsequent cyclization to the substituted 4-(phenylcarbamoyl)tetrahydro-4H-1,3,4-oxa(or thia) diazine IV' in the presence of acetic acid by the process according to the invention can be represented by the following equation:

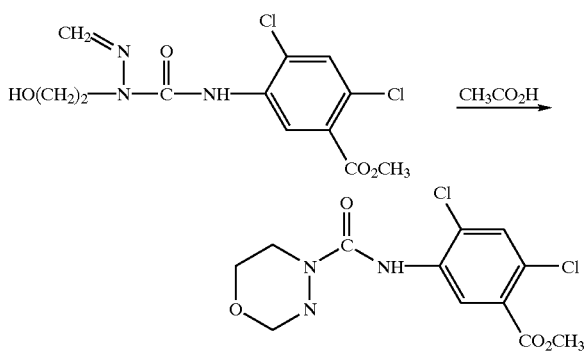

Instead of an acid, for example acetic acid, it is also possible to use a surface-active metal oxide as catalyst for the first cyclization step.

If phosgene and a further substituted 4-(phenylcarbamoyl)tetrahydro-4H-1,3,4-oxa(or thia) diazine are used, the last cyclization step to give the fused triazoles according to the invention can be represented by the following equation:

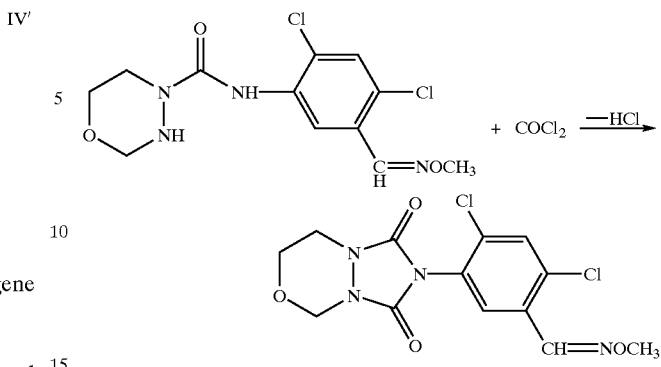

The reaction of the N-amino-N'-phenylureas II' with formaldehyde or paraformaldehyde is advantageously carried out in the presence of a solvent at 0–150° C., preferably at 10–100° C., particularly preferably at 20–60° C.

Suitable solvents for these reactions are, depending on the temperature range, hydrocarbons such as pentane, hexane, heptane, cyclohexane, aromatics, for example benzene, toluene, xylene, heteroaromatics, for example pyridine, $\alpha,\beta,\gamma$-picoline and quinoline, chlorinated hydrocarbons, for example methylene chloride, 1,1-dichloroethane, 1,2-dichloroethane, 1,1,2,2-tetrachloroethane, 1,1-dichloroethylene, chlorobenzene, 1,2-, 1,3-, 1,4-dichlorobenzene, 1-chloronaphthalene and 1,2,4-trichlorobenzene, ethers such as 1,4-dioxane, anisole, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as DMF, N-methylpyrrolidone, nitrohydrocarbons such as nitromethane, nitroethane, nitropropane and nitrobenzene, ureas such as tetraethylurea, tetrabutylurea, dimethylethyleneurea, dimethylpropyleneurea, sulfoxides such as dimethyl sulfoxide, sulfones such as dimethyl sulfone, diethyl sulfone, tetramethylene sulfone, nitriles such as acetonitrile, propionitrile, butyronitrile or isobutyronitrile; water or else mixtures of individual solvents.

The molar ratios at which the starting materials are reacted with one another are generally 0.9–1.4, preferably 0.95–1.2, particularly preferably 0.98–1.15, for the ratio of aldehyde to N-amino-N'-phenylurea II'. The concentration of the starting materials in the solvent is generally 0.1–5 mol/l, preferably 0.2–2 mol/l.

Advantageously, aqeuous formaldehyde, preferably as a 37% strength solution, is added over a period of from 2 to 20 min to a mixture of the N-amino-N'-phenylurea II' in one of the abovementioned solvents at 10–25° C., and the mixture is then stirred for another 0.5 to 12 hours, preferably for 1 to 3 hours, at 20–60° C. for the reaction to go to completion.

However, it is also possible to add the N-amino-N'-phenylurea II' to a mixture of formaldehyde in one of the abovementioned solvents and to finish the reaction as above.

Instead of aqueous formaldehyde, it is also possible to use paraformaldehyde.

It is generally not necessary to remove the water of reaction; however, the water of reaction can also be removed during the reaction using a water separator.

The reaction is carried out under exclusion of acidic catalysts, i.e. in a neutral to slightly alkaline medium. If appropriate, acidic impurities are neutralized by addition of basic compounds, for example alkali metal or alkaline earth metal hydroxides or bicarbonates or carbonates. If appropriate, it is also possible to add organic bases or to carry out the reaction using a basic cosolvent, such as pyridine.

The reaction can be carried out under atmospheric pressure or under superatmospheric pressure, either continuously or batchwise.

The cyclization of the N-methyleneimino-N'-phenylureas III' to the 4-(phenylcarbamoyl)tetrahydro-4H-1,3,4-oxa(or thia)diazines IV' is carried out with the addition of generally 1 to 100% by weight of an acid, based on III', advantageously in the presence of one of the abovementioned solvents at 0–150° C., preferably 10–120° C., particularly preferably 20–80° C.

Suitable acids are aromatic sulfonic acids, for example benzene sulfonic acid, p-chloro- or p-toluenesulfonic acid, aliphatic sulfonic acids such as methanesulfonic acid, trifluoromethanesulfonic acid, ethanesulfonic acid and n-propylsulfonic acid, sulfaminic acids such as methylsulfaminic acid, ethylsulfaminic acid or isopropylsulfaminic acid, aliphatic carboxylic acids such as acetic acid, trifluoroacetic acid, propionic acid, butyric acid or isobutyric acid, and also inorganic acids such as hydrochloric acid, sulfuric acid, nitric acid or boric acid. Advantageously, it is also possible to use an acid such as acetic acid or propionic acid directly as reaction medium.

Advantageously, the N-methyleneimino-N'-phenylurea III' is added over a period of 2–20 min at 10–25° C. to the organic acid, preferably acetic acid, as reaction medium, and stirring is continued for another 0.5 to 12 hours, preferably 1 to 3 hours, at 20–80° C. However, it is also possible to add the acid directly to the reaction solution of the N-methyleneimino-N'-phenylurea compound III' formed from N-amino-N'-phenylurea II' and formaldehyde, and to cyclize this, without isolation and, if appropriate, after incipient distillation of a solvent fraction, to give 4-(phenylcarbamoyl)tetrahydro-4H-1,3,4-oxa(or thia)diazine IV,.

The concentration of the starting materials in the solvent is generally 0.1–5 mol/l, preferably 0.2–2 mol/l.

Instead of an acid, it is also possible to use a neutral or acidic surface-active metal oxide as catalyst, for example aluminum oxide, iron oxide, boron oxide, silicon dioxide, titanium dioxide, arsenic oxide, antimony oxide, chromium oxide or manganese oxide.

The reaction can be carried out at atmospheric pressure or at superatmospheric pressure, either continuously or batchwise.

The cyclization of the 4-(phenylcarbamoyl)tetrahydro-4H-1,3,4-oxa(or thia)diazines IV' to the compounds of the formula I is carried out using phosgene or a phosgene substitute, for example diphosgene (ClC(=O)OCCl$_3$), advantageously in the presence of one of the abovementioned anhydrous solvents, at (−10)–120° C., preferably at 0–80° C., particularly preferably at 10–60° C.

Advantageously, the phosgene is introduced with stirring at 10–60° C. into a mixture of a 4-(phenylcarbamoyl)tetrahydro-4H-1,3,4-oxa(or thia)diazine IV' and an amount of 0.5–5% by weight, based on IV', of activated carbon as catalyst in one of the abovementioned anhydrous solvents over a period of 0.5–20 hours, preferably 1–12 hours.

The reaction can additionally be accelerated by a basic amide catalyst, for example dimethylformamide, which is usually employed in an amount of from 0.3 to 10% by weight, based on IV'. Suitable basic catalysts are also organic bases, such as triethylamine, tri-n-propylamine, N,N-dimethylaniline or N,N-dimethylcyclohexylamine. Preference is also given to using pyridine, if appropriate directly as solvent.

Instead of phosgene, it is also possible to use diphosgene. Advantageously, the diphosgene is added with stirring at from 0 to (−5)° C. and over a period of 2–20 min to the mixture of the starting material IV' and one of the abovementioned solvents, if appropriate with addition of activated carbon, dimethylformamide or the organic base, and the mixture is allowed to warm to 10° C. over a period of 1 hour and then stirred for another 1–12 hours at 10 to 60° C. The molar amount of phosgene or diphosgene is 0.98–5, preferably 1–3, particularly preferably 1–1.3, per mol of starting material IV'.

The concentration of the starting materials in the solvent is generally 0.1–5 mol/l, preferably 0.2–2 mol/l.

The reaction can be carried out under atmospheric pressure or under superatmospheric pressure, either continuously or batchwise.

Advantageously, the multi-step reaction can also be carried out as a one-part process where in the first step of the synthesis, in the reaction of N-amino-N'-phenylurea II' with formaldehyde, the water of reaction is removed, the N-methyleneimino-N'-phenyurea III' formed is cyclized by adding a neutral or acidic catalyst, giving the 4-(phenylcarbamoyl)tetrahydro-4H-1,3,4-oxa(or thia)diazines IV' which are then cyclized using phosgene or diphosgene, if appropriate with addition of activated carbon or an amide catalyst or in the presence of a base, to give the target compounds I'. If appropriate, any acidic catalysts which may be present are removed prior to the phosgene cyclization by phase separation or distillation, and the ring closure to give the target compounds I' is carried out subsequently.

For work-up, the intermediates III'–IV' are taken up in a water-immiscible solvent, acidic impurities or oxidizing agents are extracted using dilute alkali or water, the solution is dried and the solvent is removed under reduced pressure.

In principle, the fused triazoles I can be prepared by the synthesis process according to the invention mentioned above. However, for economic or technical reasons, it may be more advantageous to prepare some of the compounds I from similar fused triazoles which differ in the meaning of a radical.

Work-up of the reaction mixtures is usually carried out by methods known per se, for example by diluting the reaction solution with water and subsequently isolating the product by filtration, crystallization or solvent extraction, or by removing the solvent, partitioning the residue in a mixture of water and a suitable organic solvent and work-up of the organic phase to afford the product.

The fused triazoles of the formula I may contain one or more chiral centers, in which case they are usually obtained as mixtures of enantiomers or diastereomers. If desired, the mixtures can be separated into largely pure isomers using methods which are customary for this purpose, such as crystallization or chromatography, including chromatography over an optically active absorbate. Pure optically active isomers can also be prepared, for example, from suitable optically active starting materials.

Those fused triazoles where $R^{20}$=OH, $R^{22}$ and $R^{25}$=hydrogen can be converted into their salts, preferably into their alkali metal salts, in a manner known per se.

Salts of I whose metal ion is not an alkali metal ion can be prepared in a customary manner by cation exchange of the corresponding alkali metal salt, likewise ammonium, phosphonium, sulfonium or sulfoxonium hydroxides.

It is particularly advantageous to use the process according to the invention for preparing fused triazoles of the formula I in which Q is Q-1 and $R^4$ is a halogen atom, in particular fluorine. By the process described in WO 94/10173, such triazoles can be obtained only in low yield.

A mixture of different products, which can only be separated with difficulty, is usually obtained.

A further group of fused triazoles which are readily accessible by the process according to the invention are the novel fused triazoles of the formula I', which also form part of the subject matter of the present invention:

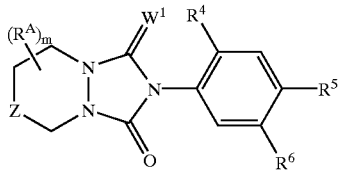

where:

Z is O, S, S=O or CO$_2$;

R$^A$ is halogen or C$_1$–C$_3$-alkyl;

W$^1$ is oxygen or sulfur;

R$^4$ is hydrogen or halogen;

R$^5$ is halogen, cyano or trifluoromethyl and

R$^6$ is a group —C(R$^{18}$)=C(R$^{19}$)—CO—R$^{20}$, —CH(R$^{18}$)—CH(R$^{19}$)—CO—R$^{20}$, —C(R$^{18}$)=C(R$^{19}$)—CO—N(R$^{20}$, R$^{21}$), —CH(R$^{18}$)—CH(R$^{19}$)—CO—N(R$^{20}$, R$^{21}$), —C(R$^{21}$)=N—OR$^{22}$, —CO—OC(R$^{23}$)(R$^{24}$)—CO—O—R$^{25}$, CO—N(R$^{26}$)—OR$^{22}$ or C(OR$^{27}$)=N—OR$^{22}$;

R$^{18}$, R$^{23}$, R$^{24}$ are each hydrogen or C$_1$–C$_3$-alkyl;

R$^{19}$ is halogen, cyano or methyl;

R$^{20}$ is hydroxyl, C$_1$–C$_6$-alkoxy, C$_3$–C$_6$-cycloalkoxy, C$_1$–C$_4$-alkoxy-C$_1$–C$_4$-alkoxy, C$_1$–C$_4$-alkylthio-C$_1$–C$_4$-alkoxy, C$_1$–C$_4$-alkylsulfinyl-CC$_1$–C$_4$-alkoxy, C$_1$–C$_4$-alkylsulfonyl-C$_1$–C$_4$-alkoxy, cyano-C$_1$–C$_6$-alkoxy, C$_1$–C$_4$-alkoxycarbonyl-C$_1$–C$_4$-alkoxy, C$_3$–C$_6$-alkenyloxy, C$_3$–C$_6$-alkynyloxy, partially or fully halogenated C$_1$–C$_6$-alkoxy, partially or fully halogenated C$_3$–C$_6$-alkenyloxy, partially or fully halogenated C$_3$–C$_6$-alkynyloxy, C$_1$–C$_6$-alkylthio, furthermore C$_1$–C$_6$-alkoxy which may carry two additional C$_1$–C$_6$-alkoxy substituents;

R$^{21}$ is hydrogen, C$_1$–C$_6$-alkyl or C$_1$–C$_6$-haloalkyl;

R$^{22}$ is hydrogen, C$_1$–C$_6$-alkyl, C$_1$–C$_4$-alkoxy-C$_1$–C$_4$-alkyl, C$_1$–C$_6$-haloalkyl, C$_1$–C$_6$-cyanoalkyl, C$_3$–C$_6$-cycloalkyl, C$_3$–C$_6$-alkenyl, C$_3$–C$_6$-alkynyl, C$_3$–C$_6$-haloalkenyl, C$_3$–C$_6$-haloalkynyl, carboxyl-CC$_1$–C$_6$-alkyl, C$_1$–C$_6$-alkoxycarbonyl-C$_1$–C$_4$-alkyl, C$_1$–C$_6$-alkylcarbonyl-C$_1$–C$_6$-alkyl or C$_1$–C$_6$-alkylcarbonyloxy-C$_1$–C$_6$-alkyl;

R$^{25}$ is hydrogen, C$_1$–C$_6$-alkyl, C$_3$–C$_6$-cycloalkyl, C$_1$–C$_6$-alkoxy-C$_1$–C$_4$-alkyl, cyano-C$_1$–C$_6$-alkyl, halo-C$_1$–C$_6$-alkyl, C$_3$–C$_6$-alkenyl or C$_3$–C$_6$-alkynyl;

R$^{26}$, R$^{27}$ independently of one another are C$_1$–C$_6$-alkyl, C$_1$–C$_4$-alkoxy-C$_1$–C$_4$-alkyl, C$_3$–C$_6$-cycloalkyl, C$_3$–C$_6$-alkenyl, C$_3$–C$_6$-alkynyl, C$_1$–C$_6$-haloalkyl, C$_1$–C$_6$-cyanoalkyl, C$_3$–C$_6$-haloalkenyl, C$_3$–C$_6$-haloalkynyl or C$_1$–C$_6$-alkoxycarbonyl-C$_1$–C$_4$-alkyl;

R$^{26}$ is additionally hydrogen and m is 0, 1, 2 or 3, and the agriculturally useful salts of the compound I.

With a view to using the fused triazoles of the invention as herbicides and/or as compounds having dessicant/defoliant action, the substituents and the index m preferably have the following meanings, in each case either on their own or in combination:

Z is oxygen;

W$^1$ is oxygen;

R$^5$ is chlorine or cyano, in particular chlorine;

R$^6$ is a group —C(R$^{18}$)=C(R$^{19}$)—CO—R$^{20}$, —CH(R$^{18}$)—CH(R$^{19}$)—CO—R$^{20}$, —C(R$^{21}$)=N—OR$^{22}$, CO—OC(R$^{23}$)(R$^{24}$)—CO—OR$^{25}$, CO—N(R$^{26}$)—OR$^{22}$ or C(O—R$^{27}$)=N—OR$^{22}$;

R$^{18}$, R$^{23}$, R$^{24}$ are each hydrogen or methyl;

R$^{19}$ is halogen or cyano;

R$^{20}$ is C$_1$–C$_6$-alkoxy, C$_3$–C$_5$-cycloalkoxy, C$_1$–C$_4$-alkoxy-C$_1$–C$_4$-alkoxy, C$_1$–C$_4$-alkoxycarbonyl-C$_1$–C$_4$-alkoxy, C$_3$–C$_6$-alkenyloxy, C$_3$–C$_6$-alkynyloxy or C$_1$–C$_4$-haloalkoxy;

R$^{21}$ is hydrogen or C$_1$–C$_4$-alkyl;

R$^{22}$ is C$_1$–C$_6$-alkyl, C$_3$–C$_6$-alkenyl, C$_3$–C$_6$-alkynyl or C$_1$–C$_6$-alkoxycarbonyl-C$_1$–C$_2$-alkyl;

R$^{25}$ is C$_1$–C$_6$-alkyl, C$_1$–C$_6$-alkoxy-C$_1$–C$_4$-alkyl, C$_3$–C$_6$-alkenyl or C$_3$–C$_6$-alkynyl;

R$^{26}$ is hydrogen, C$_1$–C$_6$-alkyl, C$_1$–C$_4$-alkoxy-C$_1$–C$_4$-alkyl, C$_3$–C$_6$-alkenyl, C$_3$–C$_6$-alkynyl or C$_1$–C$_6$-alkoxycarbonyl-C$_1$–C$_2$-alkyl;

R$^{27}$ is C$_1$–C$_6$-alkyl, C$_1$–C$_4$-alkoxy-C$_1$–C$_4$-alkyl, C$_3$–C$_6$-alkenyl, C$_3$–C$_6$-alkynyl or C$_1$–C$_6$-alkoxycarbonyl-C$_1$–C$_2$-alkyl;

m is zero.

Preferred compounds of the formula I' (where W$^1$=oxygen and R$^5$=chlorine) are listed in Table 1, fused triazoles I' where W$^1$=sulfur and R$^5$=chlorine are listed in Table 2:

TABLE 1

| Ex. No. | R$^4$ | Z | R$^6$ | Melting point or $^1$H NMR (CDCl$_3$, δ [ppm]) |
|---|---|---|---|---|
| 1.01 | H | O | —CH=N—OH | |
| 1.02 | F | O | —CH=N—OH | 189–190° C. |
| 1.03 | Cl | O | —CH=N—OH | 204–207° C. |
| 1.04 | H | O | —CH=N—OCH$_3$ | 166–168° C. |
| 1.05 | F | O | —CH=N—OCH$_3$ | 173–175° C. |
| 1.06 | Cl | O | —CH=N—OCH$_3$ | 184–185° C. |
| 1.07 | H | O | —CH=N—OC$_2$H$_5$ | |
| 1.08 | F | O | —CH=N—OC$_2$H$_5$ | |
| 1.09 | Cl | O | —CH=N—OC$_2$H$_5$ | 95–103° C. |
| 1.10 | H | O | —CH=N—OCH$_2$—C$_2$H$_5$ | |
| 1.11 | F | O | —CH=N—OCH$_2$—C$_2$H$_5$ | |

TABLE 1-continued

| Ex. No. | $R^4$ | Z | $R^6$ | Melting point or $^1$H NMR (CDCl$_3$, δ [ppm]) |
|---|---|---|---|---|
| 1.12 | Cl | O | —CH=N—OCH$_2$—C$_2$H$_5$ | |
| 1.13 | H | O | —CH=N—OCH(CH$_3$)$_2$ | |
| 1.14 | F | O | —CH=N—OCH(CH$_3$)$_2$ | |
| 1.15 | Cl | O | —CH=N—OCH(CH$_3$)$_2$ | |
| 1.16 | H | O | —CH=N—OCH$_2$—CH$_2$—OCH$_3$ | |
| 1.17 | F | O | —CH=N—OCH$_2$—CH$_2$—OCH$_3$ | |
| 1.18 | Cl | O | —CH=N—OCH$_2$—CH$_2$—OCH$_3$ | |
| 1.19 | H | O | —CH=N—OCH$_2$—CH$_2$—OC$_2$H$_5$ | |
| 1.20 | F | O | —CH=N—OCH$_2$—CH$_2$—OC$_2$H$_5$ | |
| 1.21 | Cl | O | —CH=N—OCH$_2$—CH$_2$—OC$_2$H$_5$ | |
| 1.22 | H | O | —CH=N—OCH$_2$—CO—OCH$_3$ | |
| 1.23 | F | O | —CH=N—OCH$_2$—CO—OCH$_3$ | 68–72° C. |
| 1.24 | Cl | O | —CH=N—OCH$_2$—CO—OCH$_3$ | 178–182° C. |
| 1.25 | H | O | —CH=N—OCH$_2$—CO—OC$_2$H$_5$ | |
| 1.26 | F | O | —CH=N—OCH$_2$—CO—OC$_2$H$_5$ | |
| 1.27 | Cl | O | —CH=N—OCH$_2$—CO—OC$_2$H$_5$ | |
| 1.28 | H | O | —CH=N—OCH(CH$_3$)—CO—OCH$_3$ | |
| 1.29 | F | O | —CH=N—OCH(CH$_3$)—CO—OCH$_3$ | 85–88° C. |
| 1.30 | Cl | O | —CH=N—OCH(CH$_3$)—CO—OCH$_3$ | 129–130° C. |
| 1.31 | H | O | —CH=N—OCH(CH$_3$)—CO—OC$_2$H$_5$ | |
| 1.32 | F | O | —CH=N—OCH(CH$_3$)—CO—OC$_2$H$_5$ | |
| 1.33 | Cl | O | —CH=N—OCH(CH$_3$)—CO—OC$_2$H$_5$ | |
| 1.34 | H | S | —CH=N—OH | |
| 1.35 | F | S | —CH=N—OH | |
| 1.36 | Cl | S | —CH=N—OH | |
| 1.37 | H | S | —CH=N—OCH$_3$ | |
| 1.38 | F | S | —CH=N—OCH$_3$ | |
| 1.39 | Cl | S | —CH=N—OCH$_3$ | |
| 1.40 | Cl | S | —CH=N—OC$_2$H$_5$ | |
| 1.41 | Cl | S | —CH=N—O-n-C$_3$H$_7$ | |
| 1.42 | Cl | S | —CH=N—O-i-C$_3$H$_7$ | |
| 1.43 | Cl | O | —CH=N—O—CH$_2$—CO$_2$H | |
| 1.44 | Cl | S | —CH=N—O—CH$_2$—CO$_2$H | |
| 1.45 | H | S | —CH=N—O—CH$_2$—CO$_2$CH$_3$ | |
| 1.46 | Cl | S | —CH=N—O—CH$_2$—CO$_2$CH$_3$ | |
| 1.47 | H | S | —CH=N—O—CH$_2$—CO$_2$C$_2$H$_5$ | |
| 1.48 | Cl | S | —CH=N—O—CH$_2$—CO$_2$C$_2$H$_5$ | |
| 1.49 | Cl | O | —CH=N—O—CH$_2$—CO$_2$-i-C$_3$H$_7$ | |
| 1.50 | Cl | S | —CH=N—O—CH$_2$—CO$_2$-i-C$_3$H$_7$ | |
| 1.51 | H | O | —CH=N—O—C(CH$_3$)$_2$—CO$_2$CH$_3$ | |
| 1.52 | F | O | —CH=N—O—C(CH$_3$)$_2$—CO$_2$CH$_3$ | 70-74° C. |
| 1.53 | F | O | —CH=N—O—CH$_2$—CH$_2$—Cl | |
| 1.54 | F | O | —CH=N—O—CH$_2$—CH$_2$—CH$_2$—Cl | |
| 1.55 | F | O | —CH=N—O—CHF$_2$ | |
| 1.56 | F | O | —CH=N—O—CH$_2$CF$_3$ | |
| 1.57 | F | O | —CH=N—O—CHF—CHF$_2$ | |
| 1.58 | F | O | —CH=N—O—CClF—CHF$_2$ | |
| 1.59 | F | O | —CH=N—O—CH$_2$—CCl=CH$_2$ | |
| 1.60 | F | O | —CH=N—O—CH$_2$—CH=CHCl | |
| 1.61 | F | O | —CH=N—O—CH$_2$—CCl=CHCl | |
| 1.62 | F | O | —CH=N—O—CH$_2$—CCl=CCl$_2$ | |
| 1.63 | F | O | —CH=N—O—CH$_2$—CH=CCl$_2$ | |
| 1.64 | F | S | —CH=N—O—CHF$_2$ | |
| 1.65 | F | S | —CH=N—O—CH$_2$—CH=CHCl | |
| 1.66 | F | O | —CH=N—O—CH$_2$—C≡C—Cl | |
| 1.67 | F | O | —CH=N—O—C≡C—CF$_3$ | |
| 1.68 | F | O | —CH=N—O—CH$_2$—C≡C—CH$_2$Cl | |
| 1.69 | F | O | —CH=N—O—C$_3$H$_5$ | |
| 1.70 | F | O | —CH=N—O—C$_5$H$_9$ | |
| 1.71 | F | O | —CH=N—O—C$_6$H$_{11}$ | |
| 1.72 | F | O | —CH=N—O—CH$_2$CN | |
| 1.73 | F | O | —CH=N—O—CH$_2$CH$_2$CN | |
| 1.74 | F | S | —CH=N—O—CH$_2$CN | |
| 1.75 | F | O | —CH=N—O—CH=CH$_2$ | |
| 1.76 | F | O | —CH=N—O—CH$_2$—CH=CH$_2$ | |
| 1.77 | F | O | —CH=N—O—CH(CH$_3$)—CH=CH$_2$ | |
| 1.78 | F | O | —CH=N—O—C(CH$_3$)$_2$—CH=CH$_2$ | |
| 1.79 | F | O | —CH=N—O—CH$_2$—C≡CH | 158–160° C. |
| 1.80 | F | O | —CH=N—O—CH(CH$_3$)—C≡CH | |
| 1.81 | F | O | —CH=N—O—C(CH$_3$)$_2$—C≡CH | |
| 1.82 | F | S | —CH=N—O—CH$_2$—CH=CH$_2$ | |
| 1.83 | F | S | —CH=N—O—CH(CH$_3$)—CH=CH$_2$ | |
| 1.84 | F | S | —CH=N—O—CH$_2$—C≡CH | |
| 1.85 | F | S | —CH=N—O—CH—(CH$_3$)—C≡CH | |

TABLE 1-continued

| Ex. No. | $R^4$ | Z | $R^6$ | Melting point or $^1$H NMR (CDCl$_3$, δ [ppm]) |
|---|---|---|---|---|
| 1.86 | F | O | —CH=N—O—CH$_2$—C(=O)CH$_3$ | |
| 1.87 | F | O | —CH=N—O—CH$_2$—C(=O)C$_2$H$_5$ | |
| 1.88 | F | S | —CH=N—O—CH$_2$—C(=O)CH$_3$ | |
| 1.89 | F | O | —CH=N—O—CH$_2$—O—C(=O)CH$_3$ | |
| 1.90 | F | O | —CH=N—O—CH$_2$—O—C(=O)C$_2$H$_5$ | |
| 1.91 | F | O | —CH=N—O—CH$_2$CH$_2$—O—C(=O)CH$_3$ | |
| 1.92 | Cl | S | —CH=C(Cl)—CO$_2$CH$_3$ | |
| 1.93 | Cl | S | —CH=C(Cl)—CO$_2$C$_2$H$_5$ | |
| 1.94 | H | O | —CH=C(Cl)—CO$_2$CH$_3$ | |
| 1.95 | F | O | —CH=C(Cl)—CO$_2$CH$_3$ | 158–160° C. |
| 1.96 | Cl | O | —CH=C(Cl)—CO$_2$CH$_3$ | 174–175° C. |
| 1.97 | H | O | —CH=C(Cl)—CO$_2$C$_2$H$_5$ | |
| 1.98 | F | O | —CH=C(Cl)—CO$_2$C$_2$H$_5$ | 153–155° C. |
| 1.99 | Cl | O | —CH=C(Cl)—CO$_2$C$_2$H$_5$ | |
| 1.100 | H | O | —CH=C(Cl)—CO—OCH$_2$CH$_2$—OCH$_3$ | |
| 1.101 | F | O | —CH=C(Cl)—CO—OCH$_2$CH$_2$—OCH$_3$ | |
| 1.102 | Cl | O | —CH=C(Cl)—CO—OCH$_2$CH$_2$—OCH$_3$ | |
| 1.103 | H | O | —CH=C(Cl)—CO—OCH$_2$CH$_2$—OC$_2$H$_5$ | |
| 1.104 | F | O | —CH=C(Cl)—CO—OCH$_2$CH$_2$—OC$_2$H$_5$ | |
| 1.105 | Cl | O | —CH=C(Cl)—CO—OCH$_2$CH$_2$—OC$_2$H$_5$ | |
| 1.106 | H | O | —CH=C(CH$_3$)—CO—OCH$_3$ | |
| 1.107 | F | O | —CH=C(CH$_3$)—CO—OCH$_3$ | |
| 1.108 | Cl | O | —CH=C(CH$_3$)—CO—OCH$_3$ | |
| 1.109 | H | O | —CH=C(CH$_3$)—CO—OC$_2$H$_5$ | |
| 1.110 | F | O | —CH=C(CH$_3$)—CO—OC$_2$H$_5$ | |
| 1.111 | Cl | O | —CH=C(CH$_3$)—CO—OC$_2$H$_5$ | |
| 1.112 | H | O | —CH=C(CH$_3$)—CO—OCH$_2$CH$_2$—OCH$_3$ | |
| 1.113 | F | O | —CH=C(CH$_3$)—CO—OCH$_2$CH$_2$—OCH$_3$ | |
| 1.114 | Cl | O | —CH=C(CH$_3$)—CO—OCH$_2$CH$_2$—OCH$_3$ | |
| 1.115 | H | O | —CH=C(CH$_3$)—CO—OCH$_2$CH$_2$—OC$_2$H$_5$ | |
| 1.116 | F | O | —CH=C(CH$_3$)—CO—OCH$_2$CH$_2$—OC$_2$H$_5$ | |
| 1.117 | Cl | O | —CH=C(CH$_3$)—CO—OCH$_2$CH$_2$—OC$_2$H$_5$ | |
| 1.118 | H | O | —CH=C(Br)—CO—OCH$_3$ | |
| 1.119 | F | O | —CH=C(Br)—CO—OCH$_3$ | |
| 1.120 | Cl | O | —CH=C(Br)—CO—OCH$_3$ | |
| 1.121 | H | O | —CH=C(Br)—CO—OCH$_2$CH$_2$—OC$_2$H$_5$ | |
| 1.122 | F | O | —CH=C(Br)—CO—OCH$_2$CH$_2$—OC$_2$H$_5$ | |
| 1.123 | Cl | O | —CH=C(Br)—CO—OCH$_2$CH$_2$—OC$_2$H$_5$ | |
| 1.124 | H | O | —CH=C(Br)—CO—OCH$_2$CH$_2$—OCH$_3$ | |
| 1.125 | F | O | —CH=C(Br)—CO—OCH$_2$CH$_2$—OCH$_3$ | |
| 1.126 | Cl | O | —CH=C(Br)—CO—OCH$_2$CH$_2$—OCH$_3$ | |
| 1.127 | H | O | —CH=C(Br)—CO—CCH$_2$CH$_2$—OC$_2$H$_5$ | |
| 1.128 | F | O | —CH=C(Br)—CO—OCH$_2$CH$_2$—OC$_2$H$_5$ | |
| 1.129 | Cl | O | —CH=C(Br)—CO—OCH$_2$CH$_2$—OC$_2$H$_5$ | |
| 1.130 | H | O | —CH=C(Br)—CO$_2$CH$_3$ | |
| 1.131 | H | O | —CH=C(Cl)—CO—SCH$_3$ | |
| 1.132 | H | O | —CH=C(Cl)—CO—SC$_2$H$_5$ | |
| 1.133 | H | O | —CH=C(Br)—CO—SC$_2$H$_5$ | |
| 1.134 | Cl | S | —CH=C(Cl)—CO—O—CH(CH$_3$)—CO$_2$CH$_3$ | |
| 1.135 | Cl | O | —CH=C(Cl)—CO—O—CH=CH$_2$ | |
| 1.136 | Cl | S | —CH=C(Cl)—CO—O—CH=CH$_2$ | |
| 1.137 | F | O | —CH=C(Cl)—CO—O—CH$_2$—CH=CH$_2$ | |
| 1.138 | F | O | —CH=C(Br)—CO—O—CH$_2$—CH=CH$_2$ | |
| 1.139 | Cl | O | —CH=C(Cl)—CO—O—CH(CH$_3$)—CH=CH$_2$ | |
| 1.140 | Cl | O | —CH=C(Br)—CO—O—CH(CH$_3$)—CH=CH$_2$ | |
| 1.141 | H | S | —CH=C(Cl)—CO—O—CH$_2$—CH=CH$_2$ | |
| 1.142 | F | O | —CH=C(Cl)—CO—O—CH$_2$C≡CH | |
| 1.143 | F | O | —CH=C(Cl)—CO—OC$_3$H$_5$ | |
| 1.144 | F | O | —CH=C(Cl)—CO—OC$_4$H$_7$ | |
| 1.145 | F | O | —CH=C(Cl)—CO—OC$_5$H$_9$ | |
| 1.146 | F | O | —CH=C(Cl)—CO—OC$_6$H$_{11}$ | |
| 1.147 | F | O | —CH=C(Cl)—CO—O—CH$_2$—SCH$_3$ | |
| 1.148 | F | O | —CH=C(Cl)—CO—O—CH$_2$SC$_2$H$_5$ | |
| 1.149 | F | O | —CH=C(Cl)—CO—O—CH$_2$CH$_2$—SCH$_3$ | |
| 1.150 | F | O | —CH=C(Br)—CO—O—CH$_2$CH$_2$—SCH$_3$ | |
| 1.151 | F | O | —CH=C(Cl)—CO—O—CH$_2$CH$_2$—S(O)CH$_3$ | |
| 1.152 | F | O | —CH=C(Cl)—CO—O—CH$_2$CH$_2$—SO$_2$CH$_3$ | |
| 1.153 | F | O | —CH=C(Br)—CO—O—CH$_2$CH$_2$—S(O)CH$_3$ | |
| 1.154 | F | O | —CH=C(Br)—CO—O—CH$_2$CH$_2$—SO$_2$CH$_3$ | |
| 1.155 | F | O | —CH=C(Cl)—CO—O—CH$_2$CN | |
| 1.156 | F | O | —CH=C(Cl)—CO—O—CH$_2$CH$_2$CN | |
| 1.157 | F | O | —CH=C(CH$_3$)—CO—O—CH$_2$CH$_2$CN | |
| 1.158 | F | O | —CH=C(Cl)—CO—O—CH(CH$_3$)CN | |
| 1.159 | F | O | —CH=C(Br)—CO—O—CH(CH$_3$)CH$_2$CN | |

TABLE 1-continued

| Ex. No. | R⁴ | Z | R⁶ | Melting point or ¹H NMR (CDCl₃, δ [ppm]) |
|---|---|---|---|---|
| 1.160 | F | O | —CH=C(Cl)—CO—O—CH(CH₃)CH₂CN | |
| 1.161 | F | O | —CH=C(Br)—CO—O—CH(CH₃)₂CN | |
| 1.162 | F | O | —CH=C(Br)—CO—O—C(CH₃)₂CH₂CN | |
| 1.163 | F | O | —CH=C(Cl)—CO—O—C(CH₃)₂CH₂CN | |
| 1.164 | F | O | —CH=C(Br)—CO—O—CH₂—COOCH₃ | |
| 1.165 | F | O | —CH=C(Cl)—CO—O—CH₂—COOCH₃ | 118–120° C. |
| 1.166 | F | S | —CH=C(CH₃)—CO—O—CH₂—COOCH₃ | |
| 1.167 | F | O | —CH=C(Br)—CO—O—CH(CH₃)COOCH₃ | |
| 1.168 | F | O | —CH=C(Cl)—CO—O—CH(CH₃)—COOCH₃ | 108–110° C. |
| 1.169 | F | O | —CH=C(Cl)—CO—O—C(CH₃)₂—COOCH₃ | |
| 1.170 | F | O | —CH=C(Br)—CO—O—CH₂—C≡CH | |
| 1.171 | F | O | —CH=C(Cl)—CO—O—CH₂CH₂Cl | |
| 1.172 | F | O | —CH=C(Cl)—CO—O—CH₂CF₃ | |
| 1.173 | F | O | —CH=C(Cl)—CO—O—CH(CH₃)CH₂Cl | |
| 1.174 | F | S | —CH=C(Cl)—CO—O—CH₂CH₂Cl | |
| 1.175 | F | O | —CH=C(Br)—CO—O—CH₂CH₂Cl | |
| 1.176 | F | O | —CH=C(CH₃)—CO—O—CH₂CF₃ | |
| 1.177 | F | O | —CH=C(Cl)—CO—O—CH(CH₃)CH₂Cl | |
| 1.178 | F | O | —CH=C(Cl)—CO—O—CF₂CF₃ | |
| 1.179 | F | O | —CH=C(Cl)—CO—O—CFCl—CHF₂ | |
| 1.180 | F | O | —CH=C(Cl)—CO—O—CHF—CHF₂ | |
| 1.181 | F | O | —CH=C(Cl)—CO—O—CH₂—CH=CHCl | |
| 1.182 | F | O | —CH=C(Cl)—CO—O—CH₂—C(Cl)=CH₂ | |
| 1.183 | F | O | —CH=C(Cl)—CO—O—CH₂—CH=CCl₂ | |
| 1.184 | F | O | —CH=C(Cl)—COO—CH₂—C(Cl)=CHCl | |
| 1.185 | F | O | —CH=C(Cl)—CO—O—CH₂—C≡C—Cl | |
| 1.186 | F | O | —CH=C(Cl)—CO—O—C≡C—CF₃ | |
| 1.187 | F | O | —CH=C(Cl)—CO—O—CH₂—C≡C—CH₂Cl | |
| 1.188 | F | O | —CH=C(Cl)—CO—O—CH₂—C≡C—CF₃ | |
| 1.189 | F | O | —CH=C(Cl)—COOCHCl—C≡C—CH₂Cl | |
| 1.190 | F | O | —CH=C(Br)—CO—O—CH₂—C(Cl)=CH₂ | |
| 1.191 | F | O | —CH=C(Br)—COO—CH₂—C(Cl)=CHCl | |
| 1.192 | F | O | —CH=C(Cl)—CO—O—CH₂—CH(OCH₃)₂ | |
| 1.193 | F | O | —CH=C(Br)—CO—O—CH₂—CH(OCH₃)₂ | |
| 1.194 | F | O | —CH=C(CH₃)—CO—O—CH₂—CH(OCH₃)₂ | |
| 1.195 | F | O | —CH=C(Cl)COOCH(CH₃)—CH(OCH₃)₂ | |
| 1.196 | F | O | —CH=C(Cl)—COO—CH₂CH₂CH(OCH₃)₂ | |
| 1.197 | F | O | —CH₂—CH₂—CO—OCH₃ | |
| 1.198 | F | O | —CH₂—CH₂—CO—O—C₂H₅ | |
| 1.199 | F | O | —CH₂—CH₂—CO—O-n-C₃H₇ | |
| 1.200 | F | O | —CH₂—CH₂—CO—O-n-C₄H₉ | |
| 1.201 | F | O | —CH₂—CH₂—CO—O-n-C₅H₁₁ | |
| 1.202 | F | O | —CH₂—CH(CH₃)—CO—OCH₃ | |
| 1.203 | F | O | —CH₂—CH(CH₃)—CO—OC₂H₅ | |
| 1.204 | F | O | —CH₂—CH(Cl)—CO—OC₂H₅ | |
| 1.205 | F | O | —CH₂—CH(CN)—CO—OC₂H₅ | |
| 1.206 | F | O | —CH₂—CH(Cl)—CO—O-n-C₃H₇ | |
| 1.207 | F | O | —C(CH₃)=N—OH | |
| 1.208 | F | O | —C(CH₃)=N—OCH₃ | |
| 1.209 | F | O | —C(CH₃)=N—OC₂H₅ | |
| 1.210 | F | O | —C(CH₃)=N—O-n-C₃H₇ | |
| 1.211 | F | O | —C(CH₃)=N—O—CH₂COOCH₃ | |
| 1.212 | F | O | —C(CH₃)=N—O—CH₂COOC₂H₅ | |
| 1.213 | F | O | —C(CH₃)=N—O—CH(CH₃)COOCH₃ | |
| 1.214 | F | O | —C(CH₃)=N—O—CH(CH₃)COOC₂H₅ | |
| 1.215 | F | O | —C(C₂H₅)=N—OCH₃ | |
| 1.216 | F | O | —C(C₂H₅)=N—OC₂H₅ | |
| 1.217 | F | O | —C(CH₃)=N—O—C(CH₃)₂COCH₃ | |
| 1.218 | F | O | —CO—O—CH₂—CO₂H | |
| 1.219 | F | O | —CO—O—CH₂—CO₂CH₃ | |
| 1.220 | F | O | —CO—O—CH₂—CO₂—C₂H₅ | |
| 1.221 | F | O | —CO—O—CH₂—CO₂-n-C₃H₇ | |
| 1.222 | F | O | —CO—O—CH₂—CO₂-n-C₄H₉ | |
| 1.223 | F | O | —CO—O—CH(CH₃)CO₂CH₃ | |
| 1.224 | F | O | —CO—O—CH(CH₃)CO₂C₂H₅ | |
| 1.225 | H | O | —CO—O—CH₂CO₂CH₃ | |
| 1.226 | H | O | —CO—O—CH₂CO₂C₂H₅ | |
| 1.227 | H | O | —CO—O—CH(CH₃)CO₂CH₃ | |
| 1.228 | H | S | —CO—O—CH₂CO₂CH₃ | |
| 1.229 | H | O | —CO—O—CH₂CO₂CH₂—CH=CH₂ | |
| 1.230 | F | O | —CO—O—CH₂CO₂CH₂—CH=CH₂ | |
| 1.231 | F | O | —CO—O—CH₂CO₂CH₂—C≡CH | |
| 1.232 | F | O | —CO—O—CH₂CO₂CH₂CH₂—OCH₃ | |
| 1.233 | F | O | —CO—O—CH₂CO₂CH₂CH₂—OC₂H₅ | |

TABLE 1-continued

| Ex. No. | R$^4$ | Z | R$^6$ | Melting point or $^1$H NMR (CDCl$_3$, δ [ppm]) |
|---|---|---|---|---|
| 1.234 | F | O | —CO—O—CH$_2$CO$_2$CH$_2$CH$_2$Cl | |
| 1.235 | F | O | —CO—O—CH$_2$CO$_2$CH$_2$CH$_2$CN | |
| 1.236 | F | O | —CO—O—CH(CH$_3$)CO$_2$CH$_2$—CH=CH$_2$ | |
| 1.237 | F | O | —CO—O—CH(CH$_3$)CO$_2$CH$_2$—C≡CH$_2$ | |
| 1.238 | F | O | —CO—O—CH(CH$_3$)CO$_2$CH$_2$CH$_2$—OCH$_3$ | |
| 1.239 | F | O | —CO—O—C(CH$_3$)$_2$CO$_2$CH$_3$ | |
| 1.240 | F | S | —CO—OCH$_2$CO$_2$CH$_2$—CH=CH$_2$ | |
| 1.241 | F | O | —CO—NH—OCH$_3$ | 172–174° C. |
| 1.242 | F | O | —CO—NH—OC$_2$H$_5$ | 163–165° C. |
| 1.243 | F | O | —CO—NH—O-n-C$_3$H$_7$ | |
| 1.244 | F | O | —CO—NH—O-n-C$_4$H$_9$ | |
| 1.245 | F | O | —CO—N—(CH$_3$)—OCH$_3$ | 151–153° C. |
| 1.246 | F | O | —CO—N(CH$_3$)—OC$_2$H$_5$ | 161–163° C. |
| 1.247 | F | O | —CO—N(CH$_3$)—O-n-C$_3$H$_7$ | |
| 1.248 | F | O | —CO—N(CH$_2$H$_5$)—OCH$_3$ | |
| 1.249 | F | O | —CO—N(C$_2$H$_5$)—OC$_2$H$_5$ | |
| 1.250 | F | O | —CO—N(CH$_3$)—O—CH$_2$CO$_2$CH$_3$ | |
| 1.251 | F | O | —CO—N(CH$_3$)—O—CH(CH$_3$)CO$_2$CH$_3$ | |
| 1.252 | F | O | —CO—N(CH$_3$)—O—CH$_2$CO$_2$C$_2$H$_5$ | |
| 1.253 | F | O | —CO—N(CH$_3$)—O—CH$_2$—CH=CH$_2$ | |
| 1.254 | F | O | —CO—N(CH$_3$)—O—CH$_2$—C≡CH | |
| 1.255 | F | O | —CO—N(CH$_3$)—O—CH$_2$—CH$_2$Cl | |
| 1.256 | F | O | —CO—N(CH$_3$)—O—CH$_2$—C(Cl)=CH$_2$ | |
| 1.257 | F | O | —CO—N(CH$_3$)—O—CH$_2$—CH=CHCl | |
| 1.258 | F | O | —CO—N(CH$_3$)—O—CH$_2$—C≡C—CH$_2$Cl | |
| 1.259 | F | O | —CO—N(CH$_3$)—O—CH$_2$CN | |
| 1.260 | F | O | —CO—N(CH$_3$)—O—CH$_2$CH$_2$CN | |
| 1.261 | F | O | —CO—N(CH$_3$)—O—CH$_2$—CO$_2$H | |
| 1.262 | F | O | —CO—N(CH$_3$)—O—CH(CH$_3$)—CO$_2$H | |
| 1.263 | F | O | —CO—N(CH$_3$)—O—CH$_2$—C(O)—CH$_3$ | |
| 1.264 | F | O | —CO—N(CH$_3$)—O—CH$_2$—C(O)C$_2$H$_5$ | |
| 1.265 | F | O | —CO—N(CH$_3$)—O—CH$_2$CH$_2$OC(O)CH$_3$ | |
| 1.266 | F | O | —CO—N(CH$_3$)—O—CH$_2$CH$_2$—OCH$_3$ | |
| 1.267 | F | O | —CO—N(C$_2$H$_5$)—O—CH$_2$CH$_2$—OCH$_3$ | |
| 1.268 | F | O | —CO—N(C$_2$H$_5$)—O—CH$_2$C(O)CH$_3$ | |
| 1.269 | F | O | —CO—N(C$_2$H$_5$)—O—CH$_2$CO$_2$C$_2$H$_5$ | |
| 1.270 | F | O | —CO—N(C$_2$H$_5$)—O—CH$_2$—CH=CHCl | |
| 1.271 | F | O | —CO—N(C$_2$H$_5$)—O—CH$_2$CH$_2$Cl | |
| 1.272 | F | O | —CO—N(C$_2$H$_5$)—O—CH$_2$CH$_2$CN | |
| 1.273 | F | O | —CO—N(CH$_2$—CH=CH$_2$)—OCH$_3$ | |
| 1.274 | F | O | —CO—N(CH$_2$—CH=CH$_2$)—OC$_2$H$_5$ | |
| 1.275 | F | O | —CO—N(CH$_2$—C≡CH)—OCH$_3$ | |
| 1.276 | F | O | —CO—N(CH$_2$CH$_2$Cl)—OCH$_3$ | |
| 1.277 | F | O | —CO—N(CH$_2$C(O)OCH$_3$)OCH$_3$ | |
| 1.278 | F | O | —CO—N(CH$_2$C(O)OC$_2$H$_5$)OCH$_3$ | |
| 1.279 | F | O | —CO—N(CH$_2$CH$_2$OCH$_3$)OCH$_3$ | |
| 1.280 | F | O | —CO—N(C$_3$H$_5$)OCH$_3$ | |
| 1.281 | F | O | —CO—N(CH$_2$CH$_2$CN)—O—CH$_3$ | |
| 1.282 | F | O | —CO—N(CH$_2$—CH=CHCl)—OCH$_3$ | |
| 1.283 | F | O | —CO—N(CH$_2$—C≡C—CH$_2$Cl)—OCH$_3$ | |
| 1.284 | F | O | —CO—N(CH$_2$—CH=CH$_2$)—OCH$_2$CO$_2$CH$_3$ | |
| 1.285 | F | O | —CO—N(CH$_2$—C≡CH)—OCH$_2$CO$_2$CH$_3$ | |
| 1.286 | F | O | —C(OCH$_3$)=N—OCH$_3$ | 100–105° C. |
| 1.287 | F | O | —C(OCH$_3$)=N—OC$_2$H$_5$ | 180–181° C. |
| 1.288 | F | O | —C(OCH$_3$)=N—O-n-C$_3$H$_7$ | |
| 1.289 | F | O | —C(OCH$_3$)=N—O—CH$_2$CO$_2$CH$_3$ | |
| 1.290 | F | O | —C(OCH$_3$)=N—O—CH(CH$_3$)CO$_2$CH$_3$ | |
| 1.291 | F | O | —C(OCH$_3$)=N—O—CH$_2$CO$_2$C$_2$H$_5$ | |
| 1.292 | F | O | —C(OCH$_3$)=N—O—CH$_2$CH=CH$_2$ | |
| 1.293 | F | O | —C(OCH$_3$)=N—O—CH$_2$—C≡CH | |
| 1.294 | F | O | —C(OCH$_3$)=N—O—CH$_2$CH$_2$Cl | |
| 1.295 | F | O | —C(OCH$_3$)=N—O—CH$_2$—C(Cl)=CH$_2$ | |
| 1.296 | F | O | —C(OCH$_3$)=N—O—CH$_2$—CH=CHCl | |
| 1.297 | F | O | —C(OCH$_3$)=N—O—CH$_2$—C≡C—CH$_2$Cl | |
| 1.298 | F | O | —C(OCH$_3$)=N—O—CH$_2$CN | |
| 1.299 | F | O | —C(OCH$_3$)=N—OCH$_2$CH$_2$CN | |
| 1.300 | G | O | —C(OCH$_3$)=N—O—CH$_2$CO$_2$CH$_3$ | |
| 1.301 | F | S | —C(OCH$_3$)=N—O—CH(CH$_3$)—CO$_2$CH$_3$ | |
| 1.302 | F | O | —C(OCH$_3$)=N—O—CH$_2$—C(O)CH$_3$ | |
| 1.303 | F | O | —C(OCH$_3$)=N—O—CH$_2$—C(O)C$_2$H$_5$ | |
| 1.304 | F | O | —C(OCH$_3$)=N—O—CH$_2$CH$_2$OC(O)CH$_3$ | |
| 1.305 | F | O | —C(OCH$_3$)=N—O—CH$_2$CH$_2$—OCH$_3$ | |
| 1.306 | F | O | —C(OC$_2$H$_5$)=N—O—CH$_2$CH$_2$—OCH$_3$ | |
| 1.307 | F | O | —C(OC$_2$H$_5$)=N—O—CH$_2$C(O)CH$_3$ | |

TABLE 1-continued

| Ex. No. | $R^4$ | Z | $R^6$ | Melting point or $^1$H NMR (CDCl$_3$, δ [ppm]) |
|---|---|---|---|---|
| 1.308 | F | O | —C(OC$_2$H$_5$)=N—O—CH$_2$CO$_2$C$_2$H$_5$ | |
| 1.309 | F | O | —C(OC$_2$H$_5$)=N—O—CH$_2$CH=CHCl | |
| 1.310 | F | O | —C(OC$_2$H$_5$)=N—O—CH$_2$CH$_2$Cl | |
| 1.311 | F | O | —C(OC$_2$H$_5$)=N—OCH$_2$CH$_2$CN | |
| 1.312 | F | O | —C(OCH$_2$—CH=CH$_2$)=N—OCH$_3$ | |
| 1.313 | F | O | —C(OCH$_2$—CH=CH$_2$)=N—OC$_2$H$_5$ | |
| 1.314 | F | O | —C(OCH$_2$—C≡CH)=N—OCH$_3$ | |
| 1.315 | F | O | —C(OCH$_2$CH$_2$Cl)=N—OCH$_3$ | |
| 1.316 | F | O | —C(OCH$_2$C(O)OCH$_3$)=N—OCH$_3$ | 65–70° C. |
| 1.317 | F | O | —C(OCH$_2$C(O)OC$_2$H$_5$)=N—OCH$_3$ | |
| 1.318 | F | O | —C(OCH$_2$CH$_2$OCH$_3$)=N—OCH$_3$ | |
| 1.319 | F | O | —C(OC$_3$H$_5$)=NOCH$_3$ | |
| 1.320 | Cl | O | —CH=N—O—CH$_2$CH$_2$Cl | |
| 1.321 | Cl | O | —CH=N—O—CH$_2$—CH=CHCl | |
| 1.322 | Cl | O | —CH=N—O—CH$_2$CCl=CHCl | |
| 1.323 | Cl | O | —CH=N—O—CH$_2$CCl=CCl$_2$ | |
| 1.324 | Cl | O | —CH=N—O—CH$_2$—C≡C—CH$_2$Cl | |
| 1.325 | Cl | O | —CH=N—O—C$_3$H$_5$ | |
| 1.326 | Cl | O | —CH=N—O—C$_5$H$_9$ | |
| 1.327 | Cl | O | —CH=N—O—CH$_2$CH$_2$CN | |
| 1.328 | Cl | O | —CH=N—O—CH$_2$CH=CH$_2$ | |
| 1.329 | Cl | O | —CH=N—O—CH$_2$—C≡CH | |
| 1.330 | Cl | S | —CH=N—O—CH$_2$—C≡CH | |
| 1.331 | Cl | O | —CH=N—O—CH$_2$—C(O)CH$_3$ | |
| 1.332 | Cl | O | —CH=C(Br)—CO—O—CH$_2$—CH=CH$_2$ | |
| 1.333 | Cl | O | —CH=C(Cl)—CO—O—CH$_2$—C≡CH | |
| 1.334 | Cl | O | —CH=C(Cl)—CO—O—C$_3$H$_5$ | |
| 1.335 | Cl | O | —CH=C(Cl)—CO—O—C$_5$H$_9$ | |
| 1.336 | Cl | O | —CH=C(Br)—CO—O—CH$_2$CH$_2$SCH$_3$ | |
| 1.337 | Cl | O | —CH=C(Cl)—O—CH$_2$CN | |
| 1.338 | Cl | O | —CH=C(Cl)—O—CH$_2$CH$_2$CN | |
| 1.339 | Cl | O | —CH=C(Br)—O—CH$_2$CO$_2$CH$_3$ | |
| 1.340 | Cl | O | —CH=C(Cl)—CO—O—CH(CH$_3$)—CO$_2$CH$_3$ | Ph = 8.15(s/1H), 8.03(s/1H); CH = 7.7(s/1H); CH = 5.25–5.3 (q/1H) |
| 1.341 | Cl | O | —Ch=C(Cl)—CO—O—CH$_2$CH$_2$Cl | |
| 1.342 | Cl | O | —CH=C(Cl)—CO—O—CH$_2$—CH=CHCl | |
| 1.343 | Cl | O | —CH=C(Cl)—CO—O—Ch$_2$CH(OCH$_3$)$_2$ | |
| 1.344 | Cl | O | —CH$_2$—CH$_2$—CO$_2$CH$_3$ | |
| 1.345 | Cl | O | —CH$_2$—CH$_2$—CO$_2$C$_2$H$_5$ | |
| 1.346 | Cl | O | —C(CH$_3$)=N—OCH$_3$ | |
| 1.347 | Cl | O | —C(CH$_3$)=N—O—CH$_2$CO$_2$CH$_3$ | |
| 1.348 | Cl | O | —CO—O—CH$_2$CO$_2$CH$_3$ | |
| 1.349 | Cl | O | —CO—O—CH$_2$CO$_2$C$_2$H$_5$ | |
| 1.350 | H | O | —CO—O—CH(CH$_3$)—CO$_2$C$_2$H$_5$ | |
| 1.351 | Cl | O | —CO—O—CH(CH$_3$)—CO$_2$CH$_3$ | |
| 1.352 | Cl | O | —CO—O—CH$_2$CO$_2$CH$_2$CH=CH$_2$ | |
| 1.353 | Cl | O | —CO—O—CH$_2$CO$_2$CH$_2$CH$_2$—OC$_2$H$_5$ | |
| 1.354 | Cl | O | —CO—O—C(CH$_3$)$_2$CO$_2$CH$_3$ | |
| 1.355 | F | O | —CO—O—C(CH$_3$)$_2$CO$_2$CH$_3$ | |
| 1.356 | Cl | O | —CO—O—C(CH$_3$)$_2$CO$_2$CH$_2$CH=CH$_2$ | |
| 1.357 | Cl | O | —CO—NH—OCH$_3$ | |
| 1.358 | Cl | O | —CO—NH—OC$_2$H$_5$ | |
| 1.359 | Cl | O | —CO—N(CH$_3$)—OCH$_3$ | |
| 1.360 | Cl | O | —CO—N(CH$_3$)—OC$_2$H$_5$ | |
| 1.361 | Cl | O | —CO—N(C$_2$H$_5$)—OCH$_3$ | |
| 1.362 | Cl | O | —CO—N(CH$_3$)—OCH$_2$—CH=CH$_2$ | |
| 1.363 | Cl | O | —CO—N(CH$_3$)—O—CH$_2$—CCH | |
| 1.364 | Cl | O | —CO—N(CH$_3$)—OCH$_2$CH$_2$CN | |
| 1.365 | Cl | O | —CO—N(CH$_3$)—O—CH$_2$CO$_2$CH$_3$ | |
| 1.366 | Cl | O | —CO—N(CH$_3$)—O—CH$_2$C(O)CH$_3$ | |
| 1.367 | Cl | O | —CO—N(CH$_3$)—O—CH$_2$CH$_2$OCH$_3$ | |
| 1.368 | Cl | O | —CO—N(C$_2$H$_5$)—O—CH$_2$CH$_2$—OCH$_3$ | |
| 1.369 | Cl | O | —CO—N(C$_2$H$_5$)—O—CH$_2$CO$_2$CH$_3$ | |
| 1.370 | Cl | O | —CO—N(CH$_2$—CH=CH$_2$)—OCH$_3$ | |
| 1.371 | Cl | O | —CO—N(CH$_2$CH$_2$CN)—OCH$_3$ | |
| 1.372 | Cl | O | —C(OCH$_3$)=N—OCH$_3$ | |
| 1.373 | Cl | O | —C(OCH$_3$)=N—OC$_2$H$_5$ | |
| 1.374 | Cl | O | —C(OCH$_3$)=N—O—CH$_2$CO$_2$CH$_3$ | |
| 1.375 | Cl | O | —C(OCH$_3$)=N—O—CH$_2$CO$_2$CH$_2$ | |
| 1.376 | Cl | O | —C(OCH$_3$)=N—O—CH$_2$CH$_2$Cl | |
| 1.377 | Cl | O | —C(OCH$_3$)=N—O—CH$_2$CH$_2$CN | |

TABLE 1-continued

| Ex. No. | R⁴ | Z | R⁶ | Melting point or ¹H NMR (CDCl₃, δ [ppm]) |
|---|---|---|---|---|
| 1.378 | Cl | O | —C(OCH₃)=N—O—CH₂CO₂CH₃ | |
| 1.379 | Cl | O | —C(OCH₃)=N—O—C(CH₃)₂CO₂CH₃ | |
| 1.380 | Cl | O | —C(OCH₃)=N—O—CH₂CH₂OCH₃ | |
| 1.381 | Cl | O | —C(OC₂H₅)=N—O—CH₂CH₂Cl | |
| 1.382 | Cl | O | —C(OCH₂CH=CH₂)=N—OCH₃ | |
| 1.383 | Cl | O | —C(OCH₂—C≡CH)=N—OCH₃ | |
| 1.384 | F | O | —CH=C(Cl)—CO—O-tert.C₄H₉ | 138–139° C. |
| 1.385 | F | O | —CH=C(Cl)—CO—OH | 252–253° C. |
| 1.386 | Cl | O | —CH=C(Cl)—CO—O-tert.C₄H₉ | 83–86° C. |
| 1.387 | Cl | O | —CH=C(Cl)—CO—OH | 215–220° C. |
| 1.388 | Cl | O | —CH=N—O—C(CH₃)₂CO—OCH₃ | |
| 1.389 | F | O | —CH=N—O—CH(CH₃)—CO—OCH₃ | 85–88° C. |
| 1.390 | F | O | —CH=C(Cl)—CO—NH—OCH₃ | 130° C. decomp. |
| 1.391 | F | O | —CH=C(Cl)—CO—NH—OC₂H₅ | 105–108° C. |
| 1.392 | F | O | —CH=CH—CO—OCH₃ | 198–200° C. |
| 1.393 | H | O | CO—NH—OCH₃ | 169–170° C. |
| 1.394 | H | O | CO—NH—OC₂H₅ | 163–167° C. |
| 1.395 | H | O | CO—N(CH₃)—OC₂H₅ | 71–76° C. |
| 1.396 | H | O | C(OCH₃)=N—OC₂H₅ | 90–95° C. |

TABLE 2

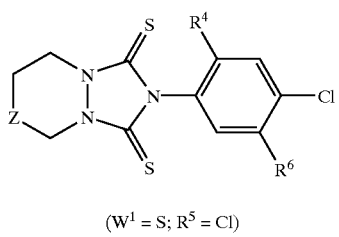

(W¹ = S; R⁵ = Cl)

| Ex. No. | Z | R⁴ | R⁶ | Melting point or ¹H-NMR |
|---|---|---|---|---|
| 1. | O | F | CH=N—OCH₃ | |
| 2. | S | F | CH=N—OCH₃ | |
| 3. | O | F | CH=N—OC₂H₅ | |
| 4. | O | F | CH=N—OCH₂—CO—OCH₃ | |
| 5. | O | F | CH=N—OCH(CH₃)—CO—OCH₃ | |
| 6. | O | F | CH=N—OC(CH₃)₂—CO—OCH₃ | |
| 7. | O | F | CH=C(Cl)—CO—OCH₃ | |
| 8. | O | F | CH=C(Cl)—CO—OC₂H₅ | |
| 9. | S | F | CH=N—OC(CH₃)₂—CO—OCH₃ | |
| 1o. | S | F | CH=C(Cl)—CO—OC₂H₅ | |
| 11. | O | F | CO—OC(CH₃)₂—CO—OCH₃ | |
| 12. | O | F | CO—OC(CH₃)₂—CO—OCH₂—CH=CH₂ | |
| 13. | S | F | CO—OC(CH₃)₂—CO—OCH₃ | |
| 14. | S | F | CO—OC(CH₃)₂—CO—OCH₂—CH=CH₂ | |
| 15. | O | F | C(OCH₃)=N—OCH₃ | |
| 16. | O | F | C(OCH₃)=N—OC₂H₅ | |
| 17. | O | F | C(OCH₃)=N—OCH₂—CO—OCH₃ | |
| 18. | S | F | C(OCH₃)=N—OCH₃ | |
| 19. | O | F | CO—OCH₂—CO—OCH₃ | |
| 20. | S | F | CO—OCH₂—CO—OCH₃ | |
| 21. | O | F | C(OCH₂—CO—OCH₃)=N—OCH₃ | |
| 22. | O | H | CH=N—OCH₃ | |
| 23. | O | H | CH=N—OC₂H₅ | |
| 24. | O | H | CH=N—OCH₂—CO—OCH₃ | |
| 25. | O | H | CH=N—OCH(CH₃)—CO—OCH₃ | |
| 26. | O | H | CH=N—OC(CH₃)₂—CO—OCH₃ | |
| 27. | O | H | CH=C(Cl)—CO—OCH₃ | |
| 28. | O | H | CH=C(Cl)—CO—OC₂H₅ | |
| 29. | O | H | CO—OC(CH₃)₂—CO—OCH₂—CH=CH₂ | |
| 30. | S | H | CO—OC(CH₃)₂—CO—OCH₂—CH=CH₂ | |

Finally, preference is also given to the fused triazoles of the formula I where X—X=—O or C—C, V=C=W², W¹ and W²=oxygen, m=zero, Q=Q⁵ where Y=oxygen, R⁷, R⁸=hydrogen and R⁹=$C_1$–$C_6$-alkoxy (=active compounds of the formula I'' where Z=oxygen or sulfur), i.e., for example, the compounds of Table 3:

TABLE 3

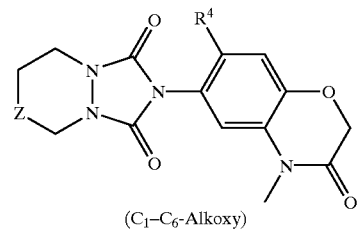

($C_1$–$C_6$-Alkoxy)

| Ex. No. | R⁴ | Z | Alkoxy radical | Melting point or ¹H-NMR |
|---|---|---|---|---|
| 3.1 | H | O | OCH₃ | |
| 3.2 | F | O | OCH₃ | |
| 3.3 | Cl | O | OCH₃ | |
| 3.4 | H | O | OC₂H₅ | |
| 3.5 | F | O | OC₂H₅ | |
| 3.6 | Cl | O | OC₂H₅ | |
| 3.7 | H | O | OCH(CH₃)₂ | |
| 3.8 | F | O | OCH(CH₃)₂ | |
| 3.9 | Cl | O | OCH(CH₃)₂ | |
| 3.10 | H | S | OCH₃ | |
| 3.11 | F | S | OCH₃ | |
| 3.12 | Cl | S | OCH₃ | |
| 3.13 | H | S | OC₂H₅ | |
| 3.14 | F | S | OC₂H₅ | |
| 3.15 | Cl | S | OC₂H₅ | |
| 3.16 | H | S | OCH(CH₃)₂ | |
| 3.17 | F | S | OCH(CH₃)₂ | |
| 3.18 | Cl | S | OCH(CH₃)₂ | |

The compounds I' and their agriculturally useful salts are suitable for use as herbicides, both in the form of isomer mixtures and in the form of the pure isomers. The herbicidal compositions comprising compounds of the formula I' are capable of controlling vegetation in non-crop areas very efficiently, especially at high rates of application. In crops such as wheat, rice, maize, soya and cotton, they act against broad-leaved weeds and grass weeds without causing any significant damage to the crop plants. This effect is observed mainly at low rates of application.

Depending on the application method employed, the compounds of the formula I', or compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. altissima, *Beta vulgaris* spec. rapa, *Brassica napus* var. napus, *Brassica napus* var. napobrassica, *Brassica rapa* var. silvestris, *Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa,* Musa spec., *Nicotiana tabacum* (*N.rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and Zea mays.

In addition, the compounds of the formula I' can also be used in crops which tolerate the action of herbicides owing to breeding including genetic engineering methods.

The active ingredients or the herbicidal compositions can be applied pre- or post-emergence. If the active ingredients are less well tolerated by certain crop plants, application techniques may be used in which the herbicidal compositions are sprayed, with the aid of spraying apparatus, in such a way that they come into as little contact as possible, if any, with the leaves of the sensitive crop plants, while the active ingredients reach the leaves of undesirable plants which grow underneath, or the exposed soil surface (post-directed, lay-by).

The compounds of the formula I', or the herbicidal compositions comprising them, can be used for example in the form of directly sprayable aqueous solutions, powders, suspensions, also highly concentrated aqueous, oily or other suspensions or dispersions, emulsions, oil dispersions, pastes, dusts, materials for spreading or granules by means of spraying, atomizing, dusting, spreading or watering. The use forms depend on the intended purposes; in any case, they should ensure the finest possible distribution of the active ingredients according to the invention.

Suitable inert additives are essentially: mineral oil fractions of medium to high boiling point, such as kerosine or diesel oil, further coal tar oils and oils of vegetable or animal origin, aliphatic, cyclic and aromatic hydrocarbons, eg. paraffin, tetrahydronaphthalene, alkylated naphthalenes or their derivatives, alkylated benzenes or their derivatives, alcohols such as methanol, ethanol, propanol, butanol, cyclohexanol, ketones such as cyclohexanone, or strongly polar solvents, eg. amines, such as N-methylpyrrolidone, or water.

Aqueous use forms can be prepared from emulsion concentrates, suspensions, pastes, wettable powders or water-dispersible granules by adding water. To prepare emulsions, pastes or oil dispersions, the fused triazoles, as such or dissolved in an oil or solvent, can be homogenized in water by means of a wetting agent, tackifier, dispersant or emulsifier. Alternatively, it is possible to prepare concentrates composed of active substance, wetting agent, tackifier, dispersant or emulsifier and, if desired, solvent or oil, these concentrates being suitable for dilution with water.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and the salts of sulfated hexa-, hepta- and octadecanols and of fatty alcohol glycol ether, condensates of sulfonated naphthalene and its derivatives with formaldehyde, condensates of naphthalene or of naphthalenesulfonic acids, with phenol and formaldehyde, polyoxyethylene octylphenol ether, ethoxylated isooctyl-, octyl- or nonylphenol, alkylphenyl polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or grinding the active substances with a solid carrier.

Granules, eg. coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders, or other solid carriers. The concentrations of the active ingredients of the formula I' in the ready-to-use preparations can be varied within wide ranges. In general, the formulations comprise from 0.001 to 98% by weight, preferably 0.01 to 95% by weight, of at least one active ingredient. The active ingredients are employed in a purity of from 90% to 100%, preferably 95% to 100% (according to NMR 40 spectrum).

Compounds I' according to the invention can be illustrated, for example as follows:

I. 20 parts by weight of the compound No. 1.05 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

II. 20 parts by weight of the compound No. 1.23 are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

III. 20 parts by weight of the active ingredient No. 1.79 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

IV. 20 parts by weight of the active ingredient No. 1.23 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel and the mixture is ground in a hammer mill. Finely distributing the mixture in 20,000 parts by weight of water gives a spray mixture which comprises 0.1% by weight of the active ingredient.

IV. 3 parts by weight of the active ingredient No. 1.05 are mixed with 97 parts by weight of finely divided kaolin. This gives a dust which comprises 3% by weight of the active ingredient.

VI. 20 parts by weight of the active ingredient No. 1.95 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound 1.98 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound 1.02 is dissolved in a mixture composed of 80 parts by weight of cyclohexanone and 20 parts by weight of Wettols® 31 (=nonionic emulsifier based on ethoxylated castor oil). This gives a stable emulsion concentrate.

To widen the spectrum of action and to achieve synergistic effects, the fused triazoles can be mixed with a large number of representatives of other groups of herbicidal or growth-regulating active ingredients and applied jointly. Suitable components for mixtures are, for example, 1,2,4-thiadiazoles, 1,3,4-thiadiazoles, amides, aminophosphoric acid and its derivatives, aminotriazoles, anilides, (het) aryloxyalkanoic acid and its derivatives, benzoic acid and its derivatives, benzothiadiazinones, 2-aroyl-1,3-cyclohexanediones, hetaryl aryl ketones, benzylisoxazolidinones, meta—$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- or hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Furthermore, it may be advantageous to employ the compounds of the formula I', on their own or in combination with other herbicides, also in a mixture with other crop protection agents, for example pesticides or agents for controlling phytopathogenic fungi or bacteria. Also of interest is the miscibility with mineral salt solutions which are employed for treating nutritional and trace element deficiencies. Nonphytotoxic oils and oil concentrates may also be added.

Depending on the intended purpose, the season, the target plants and the growth stage, the rates of application of active ingredient are from 0.001 to 3.0, preferably 0.01 to 1.0, kg of active substance (a.s.) per ha.

EXAMPLE 1 a) N-Amino-N-2-hydroxyethyl-N'-(4-chloro-2-fluoro-5-methoxy-iminomethylphenyl)urea At 0–5° C., 63.8 g (0.63 mol) of triethylamine were added with stirring to a solution of 47.9 g (0.63 mol) of hydrazinoethanol in 300 ml of 1,2-dichloroethane, and the mixture was stirred for 30 min. At the same temperature, 0.63 mol (calc. 100%) of 75% pure 4-chloro-2-fluoro-5-methoxyiminomethylphenyl isocyanate suspended in 1,2-dichloroethane, were then added over a period of 1 h, and the mixture was stirred for another 12 h. The resulting precipitate was filtered off with suction and dried, giving 20.6 g (14.7% of theory) of the corresponding subst. diphenylurea of m.p. >260° C. as by-product.

Concentration of the filtrate gave 211.6 g (88.2% of theory) of the crude title compound as a yellowish resin.

H-NMR (in $(CD_3)_2SO$); δ [ppm]=3.95 (s/3) $CH_3O$; 4.9 (s/2) $NH_2$; 7.5 (d/1) Ph; 8.3 (s/1) CHO; 8.7 (d/1) Ph; 9.1 (s/1) NH.

b) N-Methyleneimino-N-2-hydroxyethyl-N'-(4-chloro-2-fluoro-5-methoxyiminomethylphenyl)urea At 22–25° C., 27.6 g (0.34 mol) of a 37% strength formaldehyde solution were added with stirring over a period of 15 min to a solution of 90.2 g (0.296 mol) of the compound obtained in step a) in 700 ml of methylene chloride, and the mixture was stirred at 23° C. for 14 h. The aqueous phase was removed and the organic phase was dried by stirring over activated carbon and magnesium sulfate. Filtration with suction through silica gel and concentration gave 83.9 g (89.6% of theory) of the title compound of m.p. 138–139° C.

c) Tetrahydro-N-(4-chloro-2-fluoro-5-methoxyiminomethylphenyl) 4H-1,3,4-oxadiazine-4-carboxamide 22.5 g (0.072 mol) of the title compound obtained in step b) were stirred in 350 ml of glacial acetic acid at 70° C. for 5 h. The resulting clear reaction solution was concentrated and the residue was dissolved in methylene chloride, washed with sodium bicarbonate solution and dried. Filtration with suction through silica gel, concentration and stirring with diisopropyl ether gave, after filtration with suction and drying, 9.7 g (42.6% of theory) of the title compound of m.p. 169–171° C.

d) 8-(4'-chloro-2'-fluoro-5'-methoxyiminomethylphenyl)-4-oxa-7,9-dioxo-1,2,8-triaza[4.3.0.]nonane (compound 1.05 from Table 1)

By the method of Example 4c, 15 g (0.0475 mol) of the compound prepared in step c) were converted into the title compound using 9.4 g (0.0474 mol) of diphosgene in 200 ml of pyridine. 14.1 g (86.9% of theory) of the title compound of m.p. 173–175° C. were obtained.

EXAMPLE 2

(Comparison)

At 22° C., 0.54 g (0.018 mol) of a 37% strength solution of formaldehyde was added with stirring to a solution of 5 g (0.0164 mol) of the compound obtained in Example 1a) and 0.5 g of p-toluenesulfonic acid in 250 ml of dichloromethane, and the mixture was stirred under reflux for 10 h. The reaction mixture was concentrated and the residue was dissolved in methylene chloride, purified with activated carbon and filtered with suction through silica gel. This gave two fractions—0.3 g as a resin which, according to the NMR spectrum, consisted predominantly of aliphatic impurities, and 3.1 g as yellowish crystals of m.p. 105–110° C. which, according to analysis by thin-layer chromatography, consisted of 11 components. According to HPLC analysis, at most 0.673 g of the compound Ic (= a yield of 12.9%) had formed. (The corresponding NMR spectrum was so irregular that evaluation was impossible). This demonstrates that, if acid is present in the first step, the desired intermediates cannot be obtained in the purity and yield required.

EXAMPLE 3 a) N-Amino-N-2-hydroxyethyl-N'-(4-chloro-2-fluoro-5-methoxy-phenyl)urea was Obtained Starting from 121 g (0.569 mol) of 4-chloro-2-fluoro-5-methoxyphenyl Isocyanate by the Method of Example 1a. 94.5 g (59.7% of Theory) of the Title Compound of m.p. 125–128° C. were Isolated b) N-Methyleneimino-N-2-hydroxyethyl-N'-(4-chloro-2-fluoro-5-methoxyphenyl)urea 27.8 g (0.1 mol) of the compound obtained in step a) and 9 g (0.11 mol) of a 37% strength aqueous solution of formaldehyde were initially charged in 500 ml of methylene chloride and stirred at 42° C. for 2 h. The reaction mixture was dried over magnesium sulfate and filtered with suction through silica gel. Concentration gave 25.6 g (84% of theory) of the title compound of m.p. 141–142° C.

c1) Tetrahydro-N-(4-chloro-2-fluoro-5-methoxyphenyl)-4H-1,3,4-oxadiazine-4-carboxamide 19.2 g (0.0663 mol) of the product prepared in step b) were stirred in 250 ml of acetic acid at 60° C. for 2 h. The reaction mixture was concentrated under reduced pressure and the residue was stirred in diisopropyl ether/pentane (2:1). Filtration with suction and drying gave 11.5 g (59.9% of theory) of the title compound of m.p. 147–150° C. A further 1.8 g (9.4% of theory) of m.p. 145–147° C. were obtained from the mother liquor by concentration and treatment as above.

c2) Tetrahydro-N-(2,4-dichloro-5-methoxyphenyl)-4H-1,3,4-oxa-diazine-4-carboxamide (Alternative to c1)

A mixture of 29.4 g (0.1 mol) of N-amino-N-2-hydroxyethyl-N'-(2,4-dichloro-5-methoxyphenyl)urea and 9 g (0.11 mol) of a 37% strength formaldehyde solution in 500 ml of methylene chloride was stirred at 42° C. for 2 h. After cooling, the reaction mixture was filtered with suction with about 300 ml of silica gel and washed with methylene chloride. Analysis by thin-layer chromatography gave a higher Rf value than that of the reaction mixture which had not been treated with silica gel and remained on the methyleneimino stage. Concentration under reduced pressure gave 27.8 g (81.8% of theory) of the title compound of m.p. 128–130° C.

EXAMPLE 4 a) N-Amino-N-2-hydroxyethyl-N'-(2,4-dichloro-5-methoxyimino-methylphenyl)urea

Was obtained by the method of Example 1a starting from 166 g (0.6776 mol) of 2,4-dichloro-5-methoxyiminomethylphenyl isocyanate. After concentration and treatment with methylene chloride, 74.6 g (34% of theory) of the title compound of m.p. 152–156° C. were isolated as the more soluble fraction. 75 g of m.p 168–200° C. remained as the less soluble fraction which, according to the NMR spectrum, contained a further 45 g (20% of theory) of the title compound. According to the NMR spectrum, the less soluble fraction additionally contained N'-2-hydroxyethyl-N-(2,4-dichloro-5-methoxyiminomethyl-phenylcarbamoyl)hydrazide as by-product.

b) Tetrahydro-N-(2,4-dichloro-5-methoxyiminomethylphenyl)-4H-1,3,4-oxadiazine-4-carboxamide A mixture of 53.5 g (0.1666 mol) of the compound obtained in step a) and 14.9 g of a 37% strength formaldehyde solution in 1 l of methylene chloride was stirred at 42° C. for 3 h. A sample was taken and gave, on precipitation with pentane, filtration with suction, washing and drying, the corresponding methyleneimino intermediate of m.p. 156–157° C.

$^1$H-NMR (in $(CD_3)_2SO$): δ [ppm]=9.3 (1/s) NH; 8.4 (1/s)=C—H; 7.8 (1/s) and 8.74 (1/s) Ar; 6.6 (1/d) and 7.05 (1/d) N=$CH_2$; 4.8 (1/t) OH, 3.98 (3/s) $CH_3O$; 3.5 (m/2) and 3.95 (m/2) $CH_2$—$CH_2$.

The reaction mixture was then mixed with 200 ml of acetic acid and stirred at 43° C. for 40 h. After cooling, the resulting precipitate was filtered off with suction, washed with a little methylene chloride and dried. This gave 23.3 g of the title compound of m.p. 222–223° C. From the filtrate, a further 13 g of m.p. 205–208° C. were isolated, giving a total yield of 65% of thoery.

c) 8-(2',4'-dichloro-5'-methoxyiminomethylphenyl)-4-oxa-7,9-dioxo-1,2,8-triaza[4.3.0.]nonane (Compound 1.06 from Table 1)

At 0 to (−5)° C., 9.8 g (0.0495 mol) of diphosgene were added with stirring over a period of 10 min to a solution of 15 g (0.045 mol) of the compound obtained in step b) in 200 ml of pyridine. The mixture was stirred at 0–10° C. for 1 h and then for 12 h with warming to 22° C., and the reaction mixture was then concentrated, taken up in methylene chloride and washed twice with water and twice with 1 N hydrochloric acid. After drying over magnesium sulfate, stirring over activated carbon and filtration with suction through silica gel, the reaction solution was concentrated. This gave 11.3 g (68% of theory) of the title compound of m.p. 184–185° C.

EXAMPLE 5

(Process)

a) N-Methyleneimino-N-2-hydroxyethyl-N'-(4-chloro-2-fluoro-5-propargyloxyphenyl)urea 5 g (16.57 mmol) of N-amino-N-2-hydroxyethyl-N'-(4-chloro-2-fluoro-5-propargyloxyphenyl)urea (yellow resin, prepared by the method of Example 1) and 1.5 g (18.23 mmol) of 37% strength formaline were initially charged in 250 ml of methylene chloride, and the mixture was stirred at 42° C. for 3 hours. After cooling, the reaction mixture was admixed with 2 tablespoonfulls of magnesium sulfate. The mixture was then chromatographed over 200 ml of silica gel. Yield: 3.77 g (72.4% of theory) of the products of value as a yellow resin.

$^1$H-NMR (in $(CD_3)_2SO$): δ [ppm]=7.55 (d/1H), 7.95 (d/1H) Ph, 6.6 (d/1H), 7.0 (d/1H) N=CH$_2$.

b) Tetrahydro-N-(4-chloro-2-fluoro-5-propargyloxyphenyl)-4H-1,3,4-oxdiazine-4-carboxamide A solution of 4.9 g (15.62 mmol) of the compound 5a in 100 ml of acetic acid was stirred for 24 hours at 60° C., after which the reaction mixture was cooled and concentrated under reduced pressure. The residue was chromatgraphed over silica gel using methylene chloride:diethyl ether (2:1). Chromatography was carried out using methylene chloride and, towards the end, ethyl acetate. Yield: 1.4 g (29% of theory) of the product of value as a yellow resin.

$^1$H-NMR (in $(CD_3)_2SO$): δ [ppm]=8.6 (s/1H) NH; 8.1 (d/1H), 7.48 (d/1H) Ph, 5.92 (t/1H) OH; 4.85 (s/2) OCH$_2$; 4.6–4.25 (m/2H), 4.9–3.6 (m/4H); 3.6 (s/1H)—C≡CH.

EXAMPLE 6

(Comparison, Process)

Tetrahydro-N-(4-chloro-2-fluoro-5-propargyloxyphenyl)-4H-1,3,4-oxdiazine-4-carboxamide 5.0 g (16.57 mmol) of the same starting material as that used in Example 5a, 1.5 g (18.23 mmol) of 37% strength formaline and 0.5 g of p-toluenesulfonic acid were stirred in methylene chloride at 42° C. for 17 hours using a Dean and Stark water separator. After cooling, the reaction mixture was concentrated partly under reduced pressure. Purification was carried out by chromatography over 200 ml of silica gel (mobile phase: initially methylene chloride, then ethyl acetate). Yield: 3.6 g of a substance mixture which, according to TLC, HPLC and NMR, consisted of 6–7 substances. According to HPLC, the mixture contained 0.74 g (14.2% of theory) of the title compound. When the column was rinsed with methanol, only p-toluenesulfonic acid was isolated.

Use Examples

The herbicidal activity of the fused triazoles of the formula I' was demonstrated by greenhouse experiments using the compound from Example 1 (1.05 from Table 1):

The culture containers used were plastic pots containing loamy sand with approximately 3.0% of humusas the substrate. The seeds of the test plants were sown separately for each species.

In the case of pre-emergence treatment, the active ingredients, which were suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants unless this was adversely affected by the active ingredients.

For the post-emergence treatment, the test plants were first grown to a plant height of from 3 to 15 cm, depending on plant habit, and only then treated with the active ingredients which had been suspended or emulsified in water. For this purpose, the test plants were either sown directly and grown in the same containers, or they were first grown separately as seedlings and transplanted into the test containers a few days prior to treatment. The rate of application for the post-emergence treatment was 0.0313 or 0.0156 kg of a.s./ha.

Dependingon the species, the plants were kept at from 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the ariel plants, and 0 means no damage or normal course of growth.

The plants used in the experiments belonged to the following species:

| Abbreviation | Scientific Name | Common Name |
|---|---|---|
| ABUTH | *Abutilon theoprasti* | velvet leaf |
| CHEAL | *Chenopodium album* | lambsquarters (goosefoot) |
| GALAP | *Galium aparine* | catchweed bedstraw |
| POLPE | *Polygonum persicaria* | ladysthumb |
| SOLNI | *Solanum nigrum* | black night-shade |
| VERSS | *Veronica* spp. | speedwell |

When the compound from Ex. 1d was examined, the following results were obtained:

| Ex. No. | 7 | 8 |
|---|---|---|
| Rate of application (kg of a.s./ha) | 0.0313 | 0.0156 |
| Test plants | | |
| ABUTH | 100 | 100 |
| CHEAL | 98 | 98 |
| GALAP | 98 | 98 |
| POLPE | 98 | 98 |
| SOLNI | 100 | 100 |
| VERSS | 100 | 100 |

These results demonstrate the potent herbicidal activity of the novel fused triazoles I'.

We claim:

1. A fused triazole of the formula I'

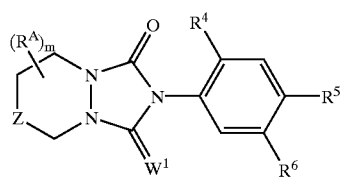

where:
Z is O;
$R^A$ is halogen or $C_1$–$C_3$-alkyl;
$W^1$ is oxygen;
$R^4$ is hydrogen or halogen;
$R^5$ is halogen, cyano or trifluoromethyl and R⁶ is a group —C(R¹⁸)═C(R¹⁹)—CO—R²⁰, —CH(R¹⁸)—CH(R¹⁹)—CO—R²⁰, —C(R¹⁸)═C(R¹⁹)—CO—N(R²⁰, R²¹), —CH(R¹⁸)—CH(R¹⁹)—C═O—N(R²⁰, R²¹), —C(R²¹)═N—O—R²², —CO—OC(R²³)(R²⁴)—CC—O—R²⁵, CO—N(R²⁶)—OR²² or C(O—R²⁷)═N—OR²²;

R¹⁸, R²³, R²⁴ are each hydrogen or $C_1$–$C_3$-alkyl;

R¹⁹ is halogen, cyano or methyl;

R²⁰ is hydroxyl, $C_1$–$C_6$-alkoxy, $C_3$–$C_6$-cycloalkoxy, $C_1$–$C_4$-alkoxy-$C_1$–$C_4$-alkoxy, $C_1$–$C_4$-alkylthio-$C_1$–$C_4$-alkoxy, $C_1$–$C_4$-alkylsulfinyl-$C_1$–$C_4$-alkoxy, $C_1$–$C_4$-alkylsulfonyl-$C_1$–$C_4$-alkoxy, cyano-$C_1$–$C_6$-alkoxy, $C_1$–$C_4$-alkoxycarbonyl-$C_1$–$C_4$-alkoxy, $C_3$–$C_6$-alkenyloxy, $C_3$–$C_6$-alkynyloxy, partially or fully halogenated $C_1$–$C_6$-alkoxy, partially or fully halogenated $C_3$–$C_6$-alkenyloxy, partially or fully halogenated $C_3$–$C_6$-alkynyloxy, $C_1$–$C_6$-alkylthio, furthermore $C_1$–$C_6$-alkoxy which may carry two additional $C_1$–$C_6$-alkoxy substituents, R²¹ is hydrogen, $C_1$–$C_6$-alkyl or $C_1$–$C_6$-haloalkyl;

R²² is hydrogen, $C_1$–$C_6$-alkyl, $C_1$–$C_4$-alkoxy-$C_1$–$C_4$-alkyl, $C_1$–$C_6$-haloalkyl, $C_1$–$C_6$-cyanoalkyl, $C_3$–$C_6$-cycloalkyl, $C_3$–$C_6$-alkenyl, $C_3$–$C_6$-alkynyl, $C_3$–$C_6$-haloalkenyl, $C_3$–$C_6$-haloalkynyl, carboxyl-$C_1$–$C_6$-alkyl, $C_1$–$C_6$-alkoxycarbonyl-$C_1$–$C_4$-alkyl, $C_1$–$C_6$-alkylcarbonyl-$C_1$–$C_6$-alkyl or $C_1$–$C_6$-alkylcarbonyloxy-$C_1$–$C_6$-alkyl;

R²⁵ is hydrogen, $C_1$–$C_6$-alkyl, $C_3$–$C_6$-cycloalkyl, $C_1$–$C_6$-alkoxy-$C_1$–$C_4$-alkyl, cyano-$C_1$–$C_6$-alkyl, halo-$C_1$–$C_6$-alkyl, $C_3$–$C_6$-alkenyl or $C_3$–$C_6$-alkynyl;

R²⁶, R²⁷ independently of one another are $C_1$–$C_6$-alkyl, $C_1$–$C_4$-alkoxy-$C_1$–$C_4$-alkyl, $C_3$–$C_6$-cycloalkyl, $C_3$–$C_6$-alkenyl, $C_3$–$C_6$-alkynyl, $C_1$–$C_6$-haloalkyl, $C_1$–$C_6$-cyanoalkyl, $C_3$–$C_6$-haloalkenyl, $C_3$–$C_6$-haloalkynyl or $C_1$–$C_6$-alkoxycarbonyl-$C_1$–$C_4$-alkyl;

R²⁶ is additionally hydrogen and m is 0, 1, 2 or 3, and the agriculturally useful salts of the compound I.

2. A fused triazole of the formula I' as claimed in claim 1, where the substituents and the index m have the following meanings:

Z is oxygen;

R⁵ is chlorine or cyano;

R¹⁸, R²³, R²⁴ are each hydrogen or methyl;

R¹⁹ is halogen or cyano;

R²⁰ is $C_1$–$C_6$-alkoxy, $C_3$–$C_5$-cycloalkoxy, $C_1$–$C_4$-alkoxy-$C_1$–$C_4$-alkoxy, $C_1$–$C_4$-alkoxycarbonyl-$C_1$–$C_4$-alkoxy, $C_3$–$C_6$-alkenyloxy, $C_3$–$C_6$-alkynyloxy or $C_1$–$C_4$-haloalkoxy;

R²¹ is hydrogen or $C_1$–$C_4$-alkyl;

R²² is $C_1$–$C_6$-alkyl, $C_3$–$C_6$-alkenyl, $C_3$–$C_6$-alkynyl or $C_1$–$C_6$-alkoxycarbonyl-$C_1$–$C_2$-alkyl;

R²⁵ is $C_1$–$C_6$-alkyl, $C_1$–$C_6$-alkoxy-$C_1$–$C_4$-alkyl, $C_3$–$C_6$-alkenyl or $C_3$–$C_6$-alkynyl;

R²⁶ is hydrogen, $C_1$–$C_6$-alkyl, $C_1$–$C_4$-alkoxy-$C_1$–$C_4$-alkyl, $C_3$–$C_6$-alkenyl, $C_3$–$C_6$-alkynyl or $C_1$–$C_6$-alkoxycarbonyl-$C_1$–$C_2$-alkyl;

R²⁷ is $C_1$–$C_6$-alkyl, $C_1$–$C_4$-alkoxy-$C_1$–$C_4$-alkyl, $C_3$–$C_6$-alkenyl, $C_3$–$C_6$-alkynyl or $C_1$–$C_6$-alkoxycarbonyl-$C_1$–$C_2$-alkyl;

m is 0, and agriculturally useful salts thereof.

3. A substituted N-methyleneimino-N'-phenylurea of the formula III'

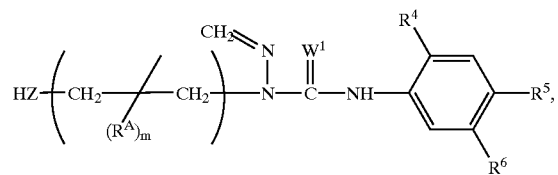

where:

Z is O;

R^A is halogen or $C_1$–$C_3$-alkyl;

m is 0, 1, 2 or 3;

W¹ is oxygen;

R⁴ is hydrogen or halogen;

R⁵ is halogen, cyano or trifluoromethyl;

R⁶ is a group —C(R¹⁸)═C(R¹⁹)—CO—R²⁰, —CH(R¹⁸)—CH(R¹⁹)—CO—R²⁰, —C(R¹⁸)═C(R¹⁹)—CO—N(R²⁰,R²¹), —CH(R¹⁸)—CH(R¹⁹)—CO—N(R²⁰,R²¹), —C(R²¹)═N—OR²², —CO—OC(R²³)(R²⁴)—CO—OR²⁵, CO—N(R²⁶)—OR²² or C(O—R²⁷)═N—OR²²;

R¹⁸, R²³, R²⁴ are each hydrogen or $C_1$–$C_3$-alkyl;

R¹⁹ is halogen, cyano or methyl;

R²⁰ is hydroxyl, $C_1$–$C_6$-alkoxy, $C_3$–$C_6$-cycloalkoxy, $C_1$–$C_4$-alkoxy-$C_1$–$C_4$-alkoxy, $C_1$–$C_4$-alkylthio-$C_1$–$C_4$-alkoxy, $C_1$–$C_4$-alkylsulfinyl-$C_1$–$C_4$-alkoxy, $C_1$–$C_4$-alkylsulfonyl-$C_1$–$C_4$-alkoxy, cyano-$C_1$–$C_6$-alkoxy, $C_1$–$C_4$-alkoxycarbonyl-$C_1$–$C_4$-alkoxy, $C_3$–$C_6$-alkenyloxy, $C_3$–$C_6$-alkynyloxy, partially or fully halogenated $C_1$–$C_6$-alkoxy, partially or fully halogenated $C_3$–$C_6$-alkenyloxy, partially or fully halogenated $C_3$–$C_6$-alkynyloxy, $C_1$–$C_6$-alkylthio, furthermore $C_1$–$C_6$-alkoxy which may carry two additional $C_1$–$C_6$-alkoxy substituents;

R²¹ is hydrogen, $C_1$–$C_6$-alkyl or $C_1$–$C_6$-haloalkyl;

R²² is hydrogen, $C_1$–$C_6$-alkyl, $C_1$–$C_4$-alkoxy-$C_1$–$C_4$-alkyl, $C_1$–$C_6$-haloalkyl, $C_1$–$C_6$-cyanoalkyl, $C_3$–$C_6$-cycloalkyl, $C_3$–$C_6$-alkenyl, $C_3$–$C_6$-alkynyl, $C_3$–$C_6$-haloalkenyl, $C_3$–$C_6$-haloalkynyl, carboxyl-$C_1$–$C_6$-alkyl, $C_1$–$C_6$-alkoxycarbonyl-$C_1$–$C_4$-alkyl, $C_1$–$C_6$-alkylcarbonyl-$C_1$–$C_6$-alkyl or $C_1$–$C_6$-alkylcarbonyloxy-$C_1$–$C_6$-alkyl;

R²⁵ is hydrogen, $C_1$–$C_6$-alkyl, $C_3$–$C_6$-cycloalkyl, $C_1$–$C_6$-alkoxy-$C_1$–$C_4$-alkyl, cyano-$C_1$–$C_6$-alkyl, halo-$C_1$–$C_6$-alkyl, $C_3$–$C_6$-alkenyl or $C_3$–$C_6$-alkynyl;

R²⁶, R²⁷ independently of one another are $C_1$–$C_6$-alkyl, $C_1$–$C_4$-alkoxy-$C_1$–$C_4$-alkyl, $C_3$–$C_6$-cycloalkyl, $C_3$–$C_6$-alkenyl, $C_3$–$C_6$-alkynyl, $C_1$–$C_6$-haloalkyl, $C_1$–$C_6$-cyanoalkyl, $C_3$–$C_6$-haloal-kenyl, $C_3$–$C_6$-haloalkynyl or $C_1$–$C_6$-alkoxycarbonyl-$C_1$–$C_4$-alkyl, and R²⁶ is additionally hydrogen.

4. A substituted N-methyleneimino-N'-phenylurea of the formula III' as claimed in claim 3, where:

Z is oxygen;

R⁵ is chlorine or cyano;

R¹⁸, R²³, R²⁴ are each hydrogen or methyl;

R¹⁹ is halogen or cyano;

R²⁰ is $C_1$–$C_6$-alkoxy, $C_3$–$C_5$-cycloalkoxy, $C_1$–$C_4$-alkoxy-$C_1$–$C_4$-alkoxy, $C_1$–$C_4$-alkoxycarbonyl-$C_1$–$C_4$-alkoxy, $C_3$–$C_6$-alkenyloxy, $C_3$–$C_6$-alkynyloxy or $C_1$–$C_4$-haloalkoxy;

$R^{21}$ is hydrogen or $C_1$–$C_4$-alkyl;

$R^{22}$ is $C_1$–$C_6$-alkyl, $C_3$–$C_6$-alkenyl, $C_3$–$C_6$-alkynyl or $C_1$–$C_6$-alkoxycarbonyl-$C_1$–$C_2$-alkyl;

$R^{25}$ is $C_1$–$C_6$-alkyl, $C_1$–$C_6$-alkoxy-$C_1$–$C_4$-alkyl, $C_3$–$C_6$-alkenyl or $C_3$–$C_6$-alkynyl;

$R^{26}$ is hydrogen, $C_1$–$C_6$-alkyl, $C_1$–$C_4$-alkoxy-$C_1$–$C_4$-alkyl, $C_3$–$C_6$-alkenyl, $C_3$–$C_6$-alkinyl or $C_1$–$C_6$-alkoxycarbonyl-$C_1$–$C_2$-alkyl;

$R^{27}$ $C_1$–$C_6$-alkyl, $C_1$–$C_4$-alkoxy-$C_1$–$C_4$-alkyl, $C_3$–$C_6$-alkenyl, $C_3$–$C_6$-alkinyl or $C_1$–$C_6$-alkoxycarbonyl-$C_1$–$C_2$-alkyl;

m is zero.

5. A fused triazole of the formula I"

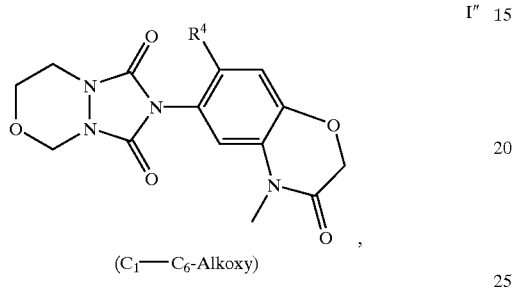

(C$_1$—C$_6$-Alkoxy)

I"

where $R^4$ is hydrogen or halogen.

6. A herbicidal composition, comprising a herbicidally effective amount of at least one fused triazole of the formula I' or an agriculturally useful salt of I' as claimed in claim 1 and at least one inert liquid and/or solid carrier and also, if desired, at least one adjuvant.

7. A composition for the dessication and/or defoliation of plants, comprising such an amount of at least one fused triazole of formula I' or an agriculturally useful salt of I' as claimed in claim 1, that acts as a dessicant and/or defoliant, and at least one inert liquid and/or solid carrier and, if desired, at least one adjuvant.

8. A method for controling undesirable vegetation, which comprises allowing a herbicidally effective amount of at least one fused trizole of the formula I' or an agriculturally useful salt of I' as claimed in claim 1, to act on plants, their habitat or on seeds.

9. A method for the dessication and/or defoliation of plants, which comprises allowing such an amount of at least one fused triazole of the formula I' or an agriculturally useful salt of I' as claimed in claim 1, to act on plants that has a dessicant and/or a defoliant action.

10. A process for preparing fused triazoles of the formula I,

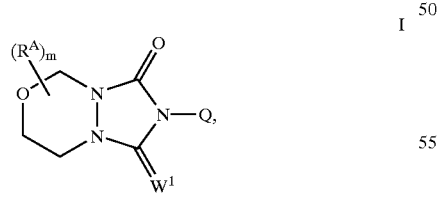

I where:

$W^1$ is oxygen or sulfur;

$R^A$ is hydrogen, hydroxyl, COOH, COOR$^2$, halogen, cyano, C(O)NR$^{11}$R$^{12}$, OR$^3$, $C_1$–$C_6$-alkyl, $C_1$–$C_6$-haloalkyl, $C_3$–$C_6$-alkenyl, $C_3$–$C_6$-alkynyl, COR$^3$, S(O)$_n$R$^3$ or C(O)SR$^2$;

$R^1$ is hydrogen, hydroxyl, halogen, CN, $C_1$–$C_6$-alkyl, $C_1$–$C_6$-haloalkyl, $C_2$–$C_6$-alkenyl, $C_2$–$C_6$-alkynyl, COR$^3$, CHO, OR$^3$, COOR$^2$, C(O)SR$^2$, C(O)NR$^{11}$R$^{12}$;

$R^2$ is hydrogen, $C_1$–$C_6$-alkyl, $C_1$–$C_6$-haloalkyl, $C_2$–$C_6$-alkenyl or $C_2$–$C_2$–$C_6$-alkynyl;

$R^3$ is $C_1$–$C_6$-alkyl, $C_3$–$C_6$-cycloalkyl, $C_2$–$C_6$-alkenyl, $C_2$–$C_6$-alkynyl, $C_1$–$C_6$-haloalkyl, $C_1$–$C_6$-alkoxy-$C_1$–$C_6$-alkyl, carboxyl-$C_1$–$C_6$-alkyl, $C_1$–$C_6$-alkoxycarbonyl-$C_1$–$C_6$-alkyl, $C_1$–$C_6$-alkylthio-$C_1$–$C_6$-alkyl, $C_1$–$C_6$-alkylsulfinyl-$C_1$–$C_6$-alkyl, $C_1$–$C_6$-alkylsulfonyl-$C_1$–$C_6$-alkyl, $C_3$–$C_6$-cycloalkyl-$C_1$–$C_6$-alkyl, $C_3$–$C_6$-alkenyloxycar-bonyl-$C_1$–$C_6$-alkyl, $C_3$–$C_6$-alkynyloxycarbonyl-$C_1$–$C_6$-alkyl, $C_3$–$C_6$-cycloalkoxy-$C_1$–$C_6$-alkyl, $C_3$–$C_6$-alkenyloxy-$C_1$–$C_6$-alkyl, $C_3$–$C_6$-alkynyloxy-$C_1$–$C_6$-alkyl, $C_1$–$C_6$-haloalkoxy-$C_1$–$C_6$-alkyl, $C_3$–$C_6$-haloalkenyloxy-$C_1$–$C_6$-alkyl, $C_3$–$C_6$-haloalkynyloxy-$C_1$–$C_6$-alkyl, $C_3$–$C_6$-cycloalkyl-$C_1$–$C_6$-thioalkyl, $C_3$–$C_6$-alkenylthio-$C_1$–$C_6$-alkyl, $C_3$–$C_6$-alkynylthio-$C_1$–$C_6$-alkyl, cyano-$C_1$–$C_6$-alkyl, $C_3$–$C_6$-halocyclo—$C_1$–$C_6$-alkyl, halo-$C_3$–$C_6$-alkenyl, $C_1$–$C_6$-alkoxy-$C_3$–$C_6$-alkenyl, $C_1$–$C_6$-haloalkoxy-$C_3$–$C_6$-alkenyl, $C_1$–$C_6$-alkylthio-$C_3$–$C_6$-alkenyl, $C_3$–$C_6$-haloalkynyl, $C_1$–$C_6$-alkoxy-$C_3$–$C_6$-alkynyl, $C_3$–$C_6$-haloalkoxyalkynyl, $C_1$–$C_6$-alkylthioalkynyl, $C_1$–$C_6$-alkyl-carbonyl, CHR$^{16}$COR$^{17}$, CHR$^{16}$P(O)(OR$^{17}$)$_2$, P(O)(OR$^{17}$)$_2$, CHR$^{16}$P(S)(OR$^{17}$)$_2$, CHR$^{16}$C(O)NR$^{11}$R$^{12}$, CHR$^{16}$C(O)NH$_2$, $C_1$–$C_6$-alkyl, which is substituted by phenoxy or benzyloxy, where the rings for their part may be substituted by halogen, $C_1$–$C_4$-alkyl or $C_1$–$C_4$-haloalkyl, benzyl which may be substituted by halogen, $C_1$–$C_4$-alkyl or $C_1$–$C_4$-haloalkyl, or is phenyl or pyridyl which may be substituted by halogen, $C_1$–$C_4$-alkyl, $C_1$–$C_4$-haloalkyl or $C_1$–$C_4$-alkoxy;

m has the value 0, 1, 2 or 3;

n has the value 0, 1 or 2;

Q is a radical Q-1:

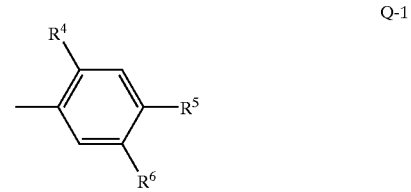

Q-1 where $R^4$ is hydrogen or halogen;

$R^5$ is $C_1$–$C_6$-alkyl, $C_1$–$C_6$-haloalkyl, OCH$_3$, SCH$_3$, OCHF$_2$, halogen, CN or NO$_2$;

$R^6$ is hydrogen, $C_1$–$C_6$-alkyl, $C_1$–$C_6$-haloalkyl, halogen, OR$^{10}$, S(O)$_n$R$^{10}$, COR$^{10}$, COOR$^{10}$, C(O)SR$^{10}$, SCH$_2$C≡CH, C(O)NR$^{11}$R$^{12}$, CHO, CH=CHCO—OR$^{10}$, CO—ON=CR$^{13}$R14, NO$_2$, CN, NHCO$_2$R$_{15}$, NHSO$_2$NHR$^{15}$, —C(R$^{18}$)=C(R$^{19}$)—CO—R$^{20}$, —CH(R$^{18}$)—CH(R$^{19}$)—CO—R$^{20}$, —C(R$^{18}$)=C(R$^{19}$)—CO—N(R$^{20}$,R$^{21}$), —CH(R$^{18}$)—CH(R$^{19}$)—CO—N(R$^{20}$,R$^{21}$), —C(R$^{21}$)=N—OR$^{22}$, —COOC(R$^{23}$)(R$^{24}$)—COOR$^{25}$, —CO—N(R$^{26}$)—OR$^{22}$ or —C(OR$^{27}$)=N—OR$^{22}$;

$R^{10}$ is one of the radicals indicated under $R^3$;

$R^{11}$, $R^{13}$ independently of one another are hydrogen or $C_1$–$C_6$-alkyl;

$R^{12}$, $R^{14}$ independently of one another are $C_1$–$C_6$-alkyl or phenyl which may be substituted by halogen, $C_1$–$C_4$-alkyl, $C_1$–$C_4$-ha-loalkyl or $C_1$–$C_4$-alkoxy;

$R^{11}$ and $R^{12}$ together may be a group —(CH$_2$)$_5$—, —(CH$_2$)$_4$— or —CH$_2$CH$_2$OCH$_2$CH$_2$— where each ring may be substituted by $C_1$–$C_3$-alkyl, or may be phenyl or benzyl;

$R^{13}$ and $R^{14}$ together with the linking carbon atom may also form a $C_3$–$C_8$-cycloalkyl group;

$R^{15}$ is $C_1$–$C_6$-alkyl or $C_1$–$C_6$-haloalkyl;

$R^{16}$ is hydrogen or $C_1$–$C_6$-alkyl;

$R^{17}$ is $C_1$–$C_6$-alkyl, $C_2$–$C_6$-alkenyl or $C_2$–$C_6$-alkynyl;

$R^{18}$, $R^{23}$, $R^{24}$ are each hydrogen or $C_1$–$C_3$-alkyl;

$R^{19}$ is halogen, cyano or methyl;

$R^{20}$ is hydroxyl, $C_1$–$C_6$-alkoxy, $C_3$–$C_6$-cycloalkoxy, $C_1$–$C_4$-alkoxy-$C_1$–$C_4$-alkoxy, $C_1$–$C_4$-alkylthio-$C_1$–$C_4$-alkoxy, $C_1$–$C_4$-alkylsulfi-nyl-$C_1$–$C_4$-alkoxy, $C_1$–$C_4$-alkylsulfonyl-$C_1$–$C_4$-alkoxy, cyano-$C_1$–$C_6$-alkoxy, $C_1$–$C_4$-alkoxycarbonyl-$C_1$–$C_4$-alkoxy, $C_3$–$C_6$-alkenyl-loxy, $C_3$–$C_6$-alkynyloxy, partially or fully halogenated $C_1$–$C_6$-alkoxy, partially or fully halogenated $C_3$–$C_6$-alkenyloxy, partially or fully halogenated $C_3$–$C_6$-alkynyloxy, $C_1$–$C_6$-alkyl-thio, furthermore $C_1$–$C_6$-alkoxy which may carry two additional $C_1$–$C_6$-alkoxy substituents, $R^{21}$ is hydrogen, $C_1$–$C_6$-alkyl or $C_1$–$C_6$-haloalkyl;

$R^{22}$ is hydrogen, $C_1$–$C_6$-alkyl, $C_1$–$C_4$-alkoxy-$C_1$–$C_4$-alkyl, $C_1$–$C_6$-ha-loalkyl, $C_1$–$C_6$-cyanoalkyl, $C_3$–$C_6$-cycloalkyl, $C_3$–$C_6$-alkenyl, $C_3$–$C_6$-alkynyl, $C_3$–$C_6$-haloalkenyl, $C_3$–$C_6$-haloalkynyl, carboxyl-$C_1$–$C_6$-alkyl, $C_1$–$C_6$-alkoxycarbonyl-$C_1$–$C_4$-alkyl, $C_1$–$C_6$-alkylcar-bonyl-$C_1$–$C_6$-alkyl or $C_1$–$C_6$-alkylcar-bonyloxy-$C_1$–$C_6$-alkyl;

$R^{25}$ is hydrogen, $C_1$–$C_6$-alkyl, $C_3$–$C_6$-cycloalkyl, $C_1$–$C_6$-alkoxy-$C_1$–$C_4$-alkyl, cyano-$C_1$–$C_6$-alkyl, halo-$C_1$–$C_6$-alkyl, $C_3$–$C_6$-alkenyl or $C_3$–$C_6$-alkynyl;

$R^{26}$, $R^{27}$ independently of one another are $C_1$–$C_6$-alkyl, $C_1$–$C_4$-alkoxy-$C_1$–$C_4$-alkyl, $C_3$–$C_6$-cycloalkyl, $C_3$–$C_6$-alkenyl, $C_3$–$C_6$-alkynyl, $C_1$–$C_6$-haloalkyl, $C_1$–$C_6$-cyanoalkyl, $C_3$–$C_6$-haloal-kenyl, $C_3$–$C_6$-haloalkynyl or $C_1$–$C_6$-alkoxycarbonyl-$C_1$–$C_4$-alkyl;

$R^{26}$ is additionally hydrogen;

which comprises reacting, in a first step, compounds of the formula II

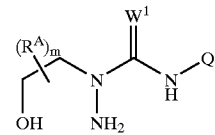

II with aqueous formaldehyde or paraformaldehyde in the absence of acids in neutral or weakly alkaline medium to give N-methylenei-mino-N'-substituted ureas of the formula III

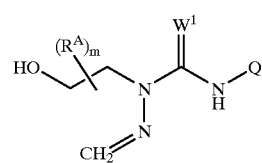

III cyclizing these subsequently in the presence of cata-lytical amounts of acid or a neutral or acidic surface-active oxide selected from the group consisting of boron oxide, silicon oxide, arsenic oxide, or anti-mony oxide, or surface active metal oxide to substi-tuted tetrahydro-4H-1,3,4-oxa(or thia)diazines of the formula IV

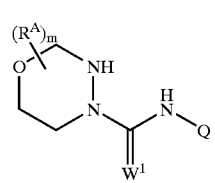

IV and cyclizing the latter with phosgene, thiophosgene or a phosgene substitute to give the compounds of the formula I.

11. A process as claimed in claim 10, wherein the surface-active metal oxide used is silica gel.

* * * * *

UNITED STATES PATENT AND TRADEMARK OFFICE
CERTIFICATE OF CORRECTION

PATENT NO. : 6,525,000 B1
DATED : February 25, 2003
INVENTOR(S) : Hamprecht et al.

It is certified that error appears in the above-identified patent and that said Letters Patent is hereby corrected as shown below:

Title page,
Item [57], ABSTRACT,
Line 3, after the formula, "$C(=V^2)$" should be -- $C(=W^2)$ --;

Column 43,
Line 5, "$(R^{24})$-CC-O-$R^{25}$" should be -- $(R^{24})$-CO-O-$R^{25}$ --;

Column 44,
Line 22, "$(R^{20},R^{21},$" should be -- $(R^{20},R^{21})$, --;
Line 54, "$C_3$-$C_6$-haloal-kenyl" should be -- $C_3$-$C_6$-haloalkenyl --;

Column 46,
Line 2, "$C_2$-$C_2$-$C_6$-alkynyl" should be -- $C_2$-$C_6$-alkynyl --;
Line 9, "alkenyloxycar-bonyl" should be -- alkenyloxycarbonyl --;
Line 21, "$C_1$-$C_6$-alkyl-carbonyl" should be -- $C_1$-$C_6$-alkylcarbonyl --;
Line 51, "R14" should be -- $R^{14}$ --;
Line 52, "$NHCO_2R_{15}$" should be -- $NHSO_2R^{15}$ --;
Line 63, "ha-loalkyl" should be -- haloalkyl --;

Column 47,
Line 12, "alkylsulfi-nyl" should be -- alkylsulfinyl --;
Line 15, "alkenyl-oxy" should be -- alkenyloxy --;
Line 18, "alkyl-thio" should be -- alkylthio --;
Line 25, "ha-loalkyl" should be -- haloalkyl --;
Line 29, "alkylcar-bonyl" should be -- alkylcarbonyl --;
Line 38, "haloal-kenyl" should be -- haloalkenyl --;

UNITED STATES PATENT AND TRADEMARK OFFICE
CERTIFICATE OF CORRECTION

PATENT NO.   : 6,525,000 B1
DATED        : February 25, 2003
INVENTOR(S)  : Hamprecht et al.

It is certified that error appears in the above-identified patent and that said Letters Patent is hereby corrected as shown below:

<u>Column 48,</u>
Line 11, "methylenei-mino" should be -- methyleneimino --.

Signed and Sealed this

Sixteenth Day of September, 2003

JAMES E. ROGAN
*Director of the United States Patent and Trademark Office*